United States Patent
Field et al.

(10) Patent No.: US 8,046,867 B2
(45) Date of Patent: **\*Nov. 1, 2011**

(54) MOBILE SURFACE CLEANER HAVING A SPARGING DEVICE

(75) Inventors: Bruce F. Field, Golden Valley, MN (US); Patrick J. Gronlund, Somerset, WI (US)

(73) Assignee: Tennant Company, Minneapolis, MN (US)

( * ) Notice: Subject to any disclaimer, the term of this patent is extended or adjusted under 35 U.S.C. 154(b) by 687 days.

This patent is subject to a terminal disclaimer.

(21) Appl. No.: 11/655,359

(22) Filed: Jan. 19, 2007

(65) Prior Publication Data

US 2007/0186367 A1    Aug. 16, 2007

Related U.S. Application Data

(60) Provisional application No. 60/864,724, filed on Nov. 7, 2006, provisional application No. 60/815,804, filed on Jun. 22, 2006, provisional application No. 60/815,721, filed on Jun. 22, 2006, provisional application No. 60/772,104, filed on Feb. 10, 2006.

(51) Int. Cl.
*A47L 7/00* (2006.01)

(52) U.S. Cl. .......................... 15/320; 15/300.1
(58) Field of Classification Search ............ 15/320; 204/80
See application file for complete search history.

(56) References Cited

U.S. PATENT DOCUMENTS

| | | | |
|---|---|---|---|
| 3,859,195 A * | 1/1975 | Williams | 204/272 |
| 3,897,320 A | 7/1975 | Cook, Jr. | |
| 3,933,614 A | 1/1976 | Bunn, Jr. | |
| 4,099,489 A | 7/1978 | Bradley | |
| 4,108,052 A | 8/1978 | Cunningham | |
| 4,121,543 A | 10/1978 | Hicks, Jr. et al. | 123/3 |
| 4,154,578 A | 5/1979 | Bane | |
| 4,244,079 A | 1/1981 | Bane | |
| 4,324,635 A | 4/1982 | Sweeney | |
| 4,374,711 A | 2/1983 | Ogawa | |
| 4,405,418 A | 9/1983 | Takemura | |
| 4,502,929 A | 3/1985 | Stewart et al. | |
| 4,603,167 A | 7/1986 | Mahalek et al. | |
| 4,630,167 A | 12/1986 | Huggins | 361/213 |
| 4,663,091 A | 5/1987 | Seo | |
| 4,670,113 A * | 6/1987 | Lewis | 205/440 |
| 4,676,882 A | 6/1987 | Okazaki | |
| 4,687,558 A | 8/1987 | Justice et al. | 204/59 |

(Continued)

FOREIGN PATENT DOCUMENTS

AU    732602    4/2001

(Continued)

OTHER PUBLICATIONS

Written Opinion dated Dec. 18, 2007 from counterpart foreign application No. PCT/US2007/003423 filed Feb. 8, 2007.

(Continued)

*Primary Examiner* — Joseph J Hail
*Assistant Examiner* — Shantese McDonald
(74) *Attorney, Agent, or Firm* — David D. Brush; Westman, Champlin & Kelly, P.A.

(57) ABSTRACT

A mobile surface cleaner is provided, which includes a mobile body configured to travel over a surface, a source of a liquid, a liquid dispenser, a flow path from the liquid source to the liquid dispenser, and an electrolyzing sparging device in fluid communication with the flow path.

30 Claims, 17 Drawing Sheets

U.S. PATENT DOCUMENTS

| | | | |
|---|---|---|---|
| 4,705,191 A | 11/1987 | Itzel et al. | |
| 4,810,344 A | 3/1989 | Okazaki | |
| 4,832,230 A | 5/1989 | Janowitz | |
| 4,875,988 A | 10/1989 | Aragon | 204/265 |
| 5,186,860 A | 2/1993 | Joyce, Jr. et al. | |
| 5,292,406 A | 3/1994 | Wanngard et al. | |
| 5,316,646 A | 5/1994 | Arai | 204/306 |
| 5,320,718 A | 6/1994 | Molter et al. | |
| 5,378,339 A | 1/1995 | Aoki et al. | |
| 5,536,389 A | 7/1996 | La Naour et al. | |
| 5,590,439 A | 1/1997 | Alazet | |
| 5,632,870 A | 5/1997 | Kucherov | |
| 5,665,212 A | 9/1997 | Zhong et al. | |
| 5,733,434 A | 3/1998 | Harada et al. | |
| 5,762,779 A | 6/1998 | Shiramizu et al. | |
| 5,766,438 A | 6/1998 | Ishibashi et al. | 204/520 |
| 5,779,891 A | 7/1998 | Andelman | |
| 5,815,869 A | 10/1998 | Hopkins | |
| 5,824,200 A | 10/1998 | Kitajima et al. | |
| 5,858,201 A | 1/1999 | Otsuka et al. | |
| 5,858,202 A | 1/1999 | Nakamura | |
| 5,928,505 A | 7/1999 | Inakagata et al. | |
| 5,931,859 A | 8/1999 | Burke | 607/66 |
| 5,997,717 A | 12/1999 | Miyashita et al. | 205/466 |
| 6,016,973 A | 1/2000 | Thompson et al. | |
| 6,032,655 A | 3/2000 | Kavonius | |
| 6,059,941 A | 5/2000 | Bryson et al. | |
| 6,088,211 A | 7/2000 | Pitel | |
| 6,101,671 A | 8/2000 | Wright et al. | |
| 6,110,353 A | 8/2000 | Hough | |
| 6,132,572 A | 10/2000 | Kim | |
| 6,200,434 B1 | 3/2001 | Shinjo et al. | |
| 6,231,747 B1 | 5/2001 | Fukuzuka et al. | |
| 6,315,886 B1 | 11/2001 | Zappi et al. | |
| 6,375,827 B1 | 4/2002 | Kurosu et al. | |
| 6,379,628 B2 | 4/2002 | de Jong et al. | |
| 6,425,958 B1 | 7/2002 | Giddings et al. | |
| 6,488,016 B2 | 12/2002 | Kavonius | |
| 6,502,766 B1 | 1/2003 | Streutker et al. | |
| 6,585,827 B2 | 7/2003 | Field et al. | |
| 6,638,364 B2 | 10/2003 | Harkins et al. | |
| 6,652,719 B1 | 11/2003 | Tseng | |
| 6,689,262 B2 | 2/2004 | Senkiw | |
| 6,703,785 B2 | 3/2004 | Aiki et al. | |
| 6,719,891 B2 | 4/2004 | Ruhr et al. | |
| 6,735,812 B2 | 5/2004 | Hekman et al. | |
| 6,842,940 B2 | 1/2005 | Christopher et al. | |
| 6,855,233 B2 | 2/2005 | Sawada | |
| 6,878,287 B1 | 4/2005 | Marais | 210/748 |
| 6,921,743 B2 | 7/2005 | Scheper et al. | |
| 6,926,819 B2 | 8/2005 | Nakamura et al. | |
| 6,964,739 B2 | 11/2005 | Boyd et al. | |
| 6,974,561 B1 | 12/2005 | Thomason | |
| 7,008,523 B2 | 3/2006 | Herrington | |
| 7,011,739 B2 | 3/2006 | Harkins et al. | |
| 7,059,013 B2 | 6/2006 | Wydra et al. | |
| 7,156,962 B2 | 1/2007 | Koizumi et al. | |
| 7,160,472 B2 | 1/2007 | Vliet et al. | |
| 7,226,542 B2 | 6/2007 | Zemel et al. | |
| 7,238,272 B2 | 7/2007 | Sano | |
| 2001/0002500 A1 | 6/2001 | Kasen et al. | |
| 2001/0034922 A1 | 11/2001 | Ko | 15/320 |
| 2002/0023847 A1* | 2/2002 | Natsume | 205/687 |
| 2002/0027070 A1 | 3/2002 | Oyokota et al. | |
| 2002/0032141 A1 | 3/2002 | Harkins | |
| 2002/0074237 A1 | 6/2002 | Takesako et al. | |
| 2002/0112314 A1 | 8/2002 | Harkins | 15/321 |
| 2002/0185423 A1 | 12/2002 | Boyd et al. | 210/167 |
| 2003/0001439 A1 | 1/2003 | Schur | 310/11 |
| 2003/0062068 A1 | 4/2003 | Ko et al. | |
| 2003/0070919 A1 | 4/2003 | Gilmore | 204/275.1 |
| 2003/0102270 A1 | 6/2003 | Schoeberl | |
| 2003/0159230 A1 | 8/2003 | Oh | |
| 2003/0159231 A1* | 8/2003 | Oh | 15/320 |
| 2003/0159233 A1 | 8/2003 | Oh | 15/321 |
| 2003/0164306 A1 | 9/2003 | Senkiw | |
| 2003/0213505 A1 | 11/2003 | Price et al. | |
| 2004/0011665 A1 | 1/2004 | Koizumi et al. | |
| 2004/0012913 A1 | 1/2004 | Andelman | |
| 2004/0037737 A1 | 2/2004 | Marais et al. | |
| 2004/0069611 A1 | 4/2004 | MacGregor | 204/157.15 |
| 2004/0112763 A1 | 6/2004 | Itoh et al. | |
| 2004/0166019 A1 | 8/2004 | Schultheiss | 422/22 |
| 2004/0168933 A1 | 9/2004 | Inoue | |
| 2004/0226123 A1 | 11/2004 | Policicchio et al. | |
| 2004/0250323 A1 | 12/2004 | Arai et al. | |
| 2004/0256247 A1 | 12/2004 | Carson et al. | |
| 2005/0121334 A1 | 6/2005 | Sumita | |
| 2005/0126928 A1 | 6/2005 | Hung et al. | |
| 2005/0136520 A1 | 6/2005 | Kinley et al. | |
| 2005/0139808 A1 | 6/2005 | Alimi | |
| 2005/1039239 | 6/2005 | Prae | |
| 2005/0194261 A1 | 9/2005 | Hadia | |
| 2005/0244556 A1 | 11/2005 | Karren | |
| 2006/0037869 A1 | 2/2006 | Mitchke | |
| 2006/0076248 A1 | 4/2006 | Kindred | |
| 2006/0162735 A1 | 7/2006 | Thiebaut | 132/200 |
| 2006/0169575 A1 | 8/2006 | Sumita | |
| 2006/0231503 A1 | 10/2006 | Flettner | 210/748 |
| 2006/0263240 A1 | 11/2006 | Hopkins | |
| 2006/0280664 A1 | 12/2006 | Huang et al. | |
| 2007/0023273 A1 | 2/2007 | Kitaori et al. | |
| 2007/0037267 A1 | 2/2007 | Lewis et al. | |
| 2007/0141434 A1 | 6/2007 | Joshi et al. | |
| 2007/0170072 A1 | 7/2007 | Shyu | |
| 2007/0186367 A1 | 8/2007 | Field et al. | |
| 2007/0186368 A1 | 8/2007 | Field et al. | |
| 2007/0186957 A1 | 8/2007 | Field et al. | |
| 2007/0186958 A1 | 8/2007 | Field et al. | |
| 2007/0187263 A1 | 8/2007 | Field et al. | |
| 2008/0264778 A1 | 10/2008 | Joshi et al. | |
| 2009/0008268 A1 | 1/2009 | Salathe et al. | |
| 2009/0127128 A1 | 5/2009 | Kitaori et al. | |
| 2009/0162505 A1 | 6/2009 | Kriebel et al. | |
| 2009/0184186 A1 | 7/2009 | Suda et al. | |
| 2009/0235481 A1 | 9/2009 | Gosebruch et al. | |
| 2010/0189805 A1 | 7/2010 | Saefkow et al. | |
| 2010/0192987 A1 | 8/2010 | Steffen et al. | |

FOREIGN PATENT DOCUMENTS

| | | |
|---|---|---|
| CN | 1440711 | 9/2003 |
| CN | 1845877 A | 10/2006 |
| CN | 200977495 Y | 11/2007 |
| DE | 2951993 | 7/1981 |
| DE | 8430251 | 6/1984 |
| DE | 8430251 U1 | 6/1984 |
| DE | 4406320 | 8/1995 |
| DE | 19752174 | 7/1998 |
| DE | 20210562 | 10/2002 |
| DE | 202004010572 U1 | 11/2004 |
| DE | 202007005471 | 6/2007 |
| DE | 202007004181 U1 | 8/2007 |
| DE | 102007017502 | 10/2008 |
| EP | 0041373 | 12/1981 |
| EP | 0104345 | 4/1984 |
| EP | 0199493 | 10/1986 |
| EP | 0438902 | 7/1991 |
| EP | 0636581 | 2/1995 |
| EP | 0663176 A1 | 7/1995 |
| EP | 0672623 | 9/1995 |
| EP | 0740329 | 10/1996 |
| EP | 761235 B1 | 3/1997 |
| EP | 1000554 B1 | 5/2000 |
| EP | 1008662 | 6/2000 |
| EP | 1162176 | 12/2001 |
| EP | 1188719 | 3/2002 |
| EP | 1293481 B1 | 3/2003 |
| EP | 1308421 | 5/2003 |
| EP | 1065170 | 1/2004 |
| EP | 1386995 | 2/2004 |
| EP | 1309519 B1 | 9/2004 |
| EP | 1533041 A1 | 5/2005 |
| EP | 1671560 | 6/2006 |
| EP | 1741676 A2 | 1/2007 |
| EP | 1754804 | 2/2007 |
| EP | 1903128 A2 | 3/2008 |
| EP | 1932809 | 6/2008 |

| | | | |
|---|---|---|---|
| EP | 1941912 A1 | 7/2008 | |
| EP | 1978142 | 10/2008 | |
| EP | 2050378 | 4/2009 | |
| EP | 2078700 | 7/2009 | |
| EP | 2078700 A1 * | 7/2009 | |
| EP | 2100623 | 9/2009 | |
| EP | 2103244 | 9/2009 | |
| EP | 2168604 | 3/2010 | |
| FR | 2381835 | 9/1978 | |
| FR | 2909370 A1 | 6/2008 | |
| GB | 611819 | 11/1948 | |
| GB | 2149423 | 11/1983 | |
| GB | 2141738 | 1/1985 | |
| GB | 2298858 | 9/1996 | |
| GB | 2381187 | 4/2003 | |
| GB | 2393737 | 4/2004 | |
| JP | 62023663 | 2/1987 | |
| JP | 1111483 | 4/1989 | |
| JP | 03157188 | 7/1991 | |
| JP | 07233493 | 9/1995 | |
| JP | 07263391 | 10/1995 | |
| JP | 08112574 | 5/1996 | |
| JP | 09075427 | 3/1997 | |
| JP | 1997174054 A | 7/1997 | |
| JP | 11090442 | 9/1997 | |
| JP | 10057282 | 3/1998 | |
| JP | 11010159 A | 1/1999 | |
| JP | 2000079393 A | 3/2000 | |
| JP | 2002-102856 | 4/2002 | |
| JP | 2002-186969 | 7/2002 | |
| JP | 2003062573 A | 3/2003 | |
| JP | 2003181338 A | 7/2003 | |
| JP | 2003261190 A | 9/2003 | |
| JP | 2003266073 A | 9/2003 | |
| JP | 2003334557 A | 11/2003 | |
| JP | 2004-073914 | 3/2004 | |
| JP | 2004-129954 | 4/2004 | |
| JP | 2004148108 A | 5/2004 | |
| JP | 2004148109 A | 5/2004 | |
| JP | 2005-535783 | 11/2005 | |
| JP | 2006-036341 | 9/2006 | |
| JP | 2007-000402 | 1/2007 | |
| JP | 2007-136356 | 6/2007 | |
| JP | 2007-239041 | 9/2007 | |
| KR | 20010096847 A | 11/2001 | |
| KR | 2002-0025023 | 11/2003 | |
| KR | 2006-0007369 | 1/2006 | |
| KR | 100599229 | 7/2006 | |
| KR | 2009-0123297 | 12/2009 | |
| NL | 1012257 C2 | 12/2000 | |
| WO | 1986006098 | 10/1986 | |
| WO | 199640591 | 12/1995 | |
| WO | 1998018723 | 5/1998 | |
| WO | WO 98/18723 | 5/1998 | |
| WO | 1998046874 | 10/1998 | |
| WO | 9908719 A2 | 2/1999 | |
| WO | 9963843 A1 | 12/1999 | |
| WO | 0015561 | 3/2000 | |
| WO | 0118279 | 3/2001 | |
| WO | 0214228 A2 | 2/2002 | |
| WO | 02066382 A1 | 8/2002 | |
| WO | 02102716 | 12/2002 | |
| WO | 2003009920 | 2/2003 | |
| WO | 2003022444 | 3/2003 | |
| WO | 2003040038 | 5/2003 | |
| WO | 2004015172 | 2/2004 | |
| WO | WO 2004/079051 | 9/2004 | |
| WO | 2004106242 A1 | 12/2004 | |
| WO | 2004108607 | 12/2004 | |
| WO | 2005014058 A1 | 2/2005 | |
| WO | 2005020780 | 3/2005 | |
| WO | 2005079468 | 9/2005 | |
| WO | 2005093129 | 10/2005 | |
| WO | 2005094904 | 10/2005 | |
| WO | 2005097350 | 10/2005 | |
| WO | 2005012186 A1 | 2/2006 | |
| WO | 2006124805 | 11/2006 | |
| WO | 20070031779 | 3/2007 | |
| WO | 2007093395 | 8/2007 | |
| WO | 2007095072 | 8/2007 | |
| WO | 2007095074 | 8/2007 | |
| WO | 2007138363 | 12/2007 | |
| WO | 2007142693 | 12/2007 | |
| WO | 2007145058 | 12/2007 | |
| WO | 2007145385 | 12/2007 | |
| WO | 2008032544 A1 | 3/2008 | |
| WO | 2008061546 A1 | 5/2008 | |
| WO | 2008131389 A1 | 10/2008 | |
| WO | 2009011841 | 1/2009 | |
| WO | 2009039674 | 4/2009 | |
| WO | 2009040407 | 4/2009 | |
| WO | 2009046563 | 4/2009 | |
| WO | 2009067838 | 6/2009 | |
| WO | 2010055108 | 5/2010 | |

OTHER PUBLICATIONS

International Preliminary Report on Patentability dated May 9, 2008 from counterpart foreign application No. PCT/US2007/003423 filed Feb. 8, 2007.
USPTO Office Action dated Jul. 16, 2009 for U.S. Appl. No. 11/655,390, filed Jan. 19, 2007.
Bluhm, Hans J. et al., "Disruption and Destruction of Biological Cells Using Strong Pulsed Electric Fields" Nachrichten, Karlsruhe, DE, vol. 3, Jan. 1, 2005, pp. 105-110.
Final Office Action from the United States Patent and Trademark Office for U.S. Appl. No. 11/655,378, dated Jul. 2, 2010.
Chinese Office Action with English Translation dated Jun. 9, 2010 for corresponding Chinese Application No. 200780010434.8, filed Feb. 8, 2007.
Office Action from the United States Patent and Trademark Office for U.S. Appl. No. 11/655,359, dated Mar. 19, 2009.
Office Action from the United States Patent and Trademark Office for U.S. Appl. No. 11/655,390, dated Jul. 16, 2009.
Office Action from the United States Patent and Trademark Office for U.S. Appl. No. 11/655,359, dated Nov. 13, 2009.
Restriction Requirement from the United States Patent and Trademark Office for U.S. Appl. No. 11/655,385, dated Dec. 9, 2009.
Final Office Action from the United States Patent and Trademark Office for U.S. Appl. No. 11/655,390, dated Jan. 11, 2010.
Office Action from the United States Patent and Trademark Office for U.S. Appl. No. 11/655,378, dated Jan. 14, 2010.
Office Action from the United States Patent and Trademark Office for U.S. Appl. No. 11/655,385, dated Jan. 29, 2010.
English Translation of Chinese Office Action for corresponding Chinese Patent Application No. 200780012999.X, dated Dec. 11, 2009.
JP-HC15022149.
"Conductive Polymers: Evaluation of Industrial Applications" Synthetic Metals, 55-57 (1993) 3623-3631 S. Roth et al.
Restriction Requirement from the United States Patent and Trademark Office for U.S. Appl. No. 11/655,390, dated Apr. 10, 2009.
Notice of Allowance from the United States Patent and Trademark Office for U.S. Appl. No. 11/655,385, dated Jul. 14, 2010.
Office Action from the United States Patent and Trademark Office for Application No. 11/655,390, dated Jul. 19, 2010.
Office Action from the United States Patent and Trademark Office for U.S. Appl. No. 11/655,365, dated Dec. 3, 2010.
Notice of Allowance from the United States Patent and Trademark Office for U.S. Appl. No. 11/655,390, dated Jan. 6, 2011.
Aoki et al., "Wafer Treatment Using Electrolysis-Ionized Water", 1994, Jpn. J. Appl. Phys. vol. 33, pp. 5686-5689.
Restriction/Election Requirement from the United States Patent and Trademark Office for U.S. Appl. No. 11/655,365, dated Aug. 17, 2010.
Office Action from the United States Patent and Trademark Office for U.S. Appl. No. 11/655,378, dated Sep. 9, 2010.
Office Action from the United States Patent and Trademark Office for U.S. Appl. No. 11/655,415, dated Sep. 29, 2010.
Office Action from the United States Patent and Trademark Office for U.S. Appl. No. 11/655,360, dated Sep. 30, 2010.
Office Action from the United States Patent and Trademark Office for U.S. Appl. No. 12/122,350, dated Sep. 30, 2010.

Office Action from the United States Patent and Trademark Office for U.S. Appl. No. 11/655,310, dated Oct. 1, 2010.
Office Action from the United States Patent and Trademark Office for U.S. Appl. No. 11/655,389, dated Oct. 1, 2010.
Communication from European Patent Office, dated Aug. 19, 2010 for corresponding European Patent Application No. 07 77 0011.0.
Final Office Action from the United States Patent and Trademark Office for U.S. Appl. No. 11/655,378, dated Jan. 25, 2011.
Notice of Allowance from the United States Patent and Trademark Office for U.S. Appl. No. 12/122,350, dated Mar. 16, 2011.
Notice of Allowance from the United States Patent and Trademark Office for U.S. Appl. No. 11/655,389, dated Mar. 17, 2011.
Notice of Allowance from the United States Patent and Trademark Office for U.S. Appl. No. 11/655,360, dated Mar. 18, 2011.
Notice of Allowance from the United States Patent and Trademark Office for U.S. Appl. No. 11/655,415, dated Mar. 23, 2011.
Notice of Allowance from the United States Patent and Trademark Office for U.S. Appl. No. 11/655,310, dated Mar. 23, 2011.
Notice of Allowability from the United States Patent and Trademark Office for U.S. Appl. No. 11/655,378, dated Apr. 28, 2011.
Notice of Allowance from the United States Patent and Trademark Office for U.S. Appl. No. 11/655,378, dated May. 10, 2011.
English translation of Japanese Office Action dated Jun. 21, 2011 for Japanese Patent Application No. 2008-554363.
English translation of Japanese Office Action dated Jun. 2, 2011 for Japanese Patent Application No. 2008-554377.
English translation of Japanese Office Action dated May 25, 2011 from Japanese Application No. 2008-554350.
Mexican Office Action dated May 25, 2011 from Mexican Application No. MX/a/2008/010114.

"Fast-Foam Scrubbing Technology, The Safe Scrubbing Alternative,T5-Parts Manual," Tennant Company, www.tennantco.com, 2006.
"Fast-Foam Scrubbing Technology, The Safe Scrubbing Alternative, T5-Scrubber-Dryer Operator Manual," Tennant Company, www.tennantco.com, 2006.
"Eco Smarte-The Best Multiple Mineral Technology for Problem Well Water; The Best Chemical Reduction System for City Water Complete Bacteria and Scale Control," ECOsmarte® Planet Friendly, Inc., http://www.ecosmarte.com/sciencesummary.html, 1994, pp. 1-13.
"KREBS Engineers® Products," 2006 Krebs Engineers, httpP//www.krebs.com/about.php/ and http://www.krebs.com/products/php/product/20/CycloClean%AE+Modules, 2006, pp. 1-3.
"The Oxygenator Livelier Bait-Healthier fish," Aqua Innovations, Inc., aquainnovationsinc.com, published prior to Jan. 19, 2007, pp. 1-2.
"JP102 Water Cell," Emco Tech Co., Ltd. of Goyang-City Kyungki-Do, South Korea, Oct. 18, 2006, pp. 1.
Mary Jones, "Richfield-Based EcoSmarte has Perfected a Natural- and Profitable-Approach to Water Purification," Minnesota Technology, Inside Technology and Manufacturing Business, Fall 2005, pp. 1-3.
Notification of Transmittal of the International Search Report and the Written Opinion of the International Searching Authority, or the Declaration in counterpart foreign application No. PCT/US2007/003423 filed Feb. 8, 2007.

* cited by examiner

MOBILE SURFACE CLEANER HAVING A SPARGING DEVICE

CROSS-REFERENCE TO RELATED APPLICATIONS

This application claims priority from and the benefit of the following U.S. Provisional Applications: 60/772,104, filed Feb. 10, 2006 and entitled "ELECTROCHEMICALLY ACTIVATED WATER FOR HARD AND SOFT FLOOR CLEANING SYSTEMS;" 60/815,804, filed Jun. 22, 2006 and entitled "ELECTROCHEMICALLY ACTIVATED WATER FOR HARD AND SOFT FLOOR CLEANING SYSTEMS;" 60/815,721, filed Jun. 22, 2006 and entitled "METHOD AND APPARATUS FOR THE GENERATION AND USE OF SPARGED ELECTROCHEMICALLY ACTIVATED LIQUID;" and 60/864,724, filed Nov. 7, 2006 and entitled "METHOD AND APPRATAUS FOR THE GENERATION AND USE OF ELECTROCHEMICALLY ACTIVATED LIQUID WITH VISUAL INDICATOR," which are incorporated herein by reference in their entireties.

Cross-reference is also made to the following U.S. Patent Applications, which were filed on even date herewith and are hereby incorporated by reference in their entireties: U.S. application Ser. No. 11/655,365, entitled "CLEANING APPARATUS HAVING A FUNCTIONAL GENERATOR FOR PRODUCING ELECTROCHEMICALLY ACTIVATED CLEANING LIQUID;" U.S. application Ser. No. 11/655,389, entitled "METHOD FOR GENERATING ELECTROCHEMICALLY ACTIVATED CLEANING LIQUID;" U.S. application Ser. No. 11/655,360, entitled "METHOD OF PRODUCING A SPARGED CLEANING LIQUID ONBOARD A MOBILE SURFACE CLEANER;" U.S. application Ser. No. 11/655,390, entitled "APPARATUS FOR GENERATING SPARGED, ELECTROCHEMICALLY ACTIVATED LIQUID;" U.S. application Ser. No. 11/655,310, entitled "METHOD OF GENERATING SPARGED, ELECTROCHEMICALLY ACTIVATED LIQUID;" U.S. application Ser. No. 11/655,385, entitled "METHOD AND APPARATUS FOR PRODUCING HUMANLY-PERCEPTABLE INDICATOR OF ELECTROCHEMICAL PROPERTIES OF AN OUTPUT CLEANING LIQUID;" U.S. application Ser. No. 11/655,378, entitled "ELECTROCHEMICALLY ACTIVATED ANOLYTE AND CATHOLYTE LIQUID;" U.S. application Ser. No. 11/655,415, entitled "METHOD AND APPARATUS FOR GENERATING, APPLYING AND NEUTRALIZING AN ELECTROCHEMICALLY ACTIVATED LIQUID."

FIELD OF THE DISCLOSURE

The present disclosure relates to cleaning and/or sanitizing systems, and more particularly but not limited to systems that generate a working liquid having cleaning and/or sanitizing properties.

BACKGROUND OF THE DISCLOSURE

A wide variety of systems are in use today for cleaning or disinfecting residential, industrial, commercial, hospital, food processing, and restaurant facilities, such as surfaces and other substrates, and for cleaning or disinfecting various items, such as food products or other articles.

For example, hard floor surface scrubbing machines are widely used to clean the floors of industrial and commercial buildings. They range in size from a small model, which is controlled by an operator walking behind it, to a large model, which is controlled by an operator riding on the machine. Such machines in general are wheeled vehicles with suitable operator controls. Their bodies contain power and drive elements, a solution tank to hold a cleaning liquid, and a recovery tank to hold soiled solution recovered from the floor being scrubbed. A scrub head, which contains one or more scrubbing brushes and associated drive elements are attached to the vehicle and may be located in front of, under or behind it. A solution distribution system dispenses cleaning liquid from the solution tank to the floor in the vicinity of the scrubbing brush or brushes.

Soft floor cleaning machines can be implemented as small mobile machines that are handled by an operator or can be implemented in a truck-mounted system having a cleaning wand connected to the truck. The truck carries a cleaning liquid solution tank, a wastewater recovery tank and a powerful vacuum extractor.

Typical cleaning liquids used in hard and soft floor cleaning systems include water and a chemically based detergent. The detergent typically includes a solvent, a builder, and a surfactant. While these detergents increase cleaning effectiveness for a variety of different soil types, such as dirt and oils, these detergents also have a tendency to leave unwanted residue on the cleaned surface. Such residue can adversely affect the appearance of the surface and the tendency of the surface to re-soil and, depending on the detergent, can potentially cause adverse health or environment effects. Similar disadvantages apply to cleaning systems for other types of surfaces and items.

Improved cleaning systems are desired for reducing the use of typical detergents and/or reducing the residue left on the surface after cleaning while maintaining desired cleaning and/or disinfecting properties.

SUMMARY

An embodiment of the disclosure is directed to a mobile surface cleaner. The cleaner includes a mobile body configured to travel over a surface, a source of a liquid, a liquid dispenser, a flow path from the liquid source to the liquid dispenser, and an electrolyzing sparging device in fluid communication with the flow path.

Another embodiment is directed to a mobile surface cleaner. The cleaner includes a mobile body configured to travel over a surface, a tank carried by the mobile body, a motorized cleaning head connected to the mobile body and comprising a cleaning tool, a liquid dispenser, a flow path from the tank to the liquid dispenser, and an electrolyzer onboard the cleaner, which sparges the liquid by electrolysis.

Another embodiment is directed to a mobile surface cleaner. The cleaner includes a mobile body configured to travel over a surface, a source of a liquid, a liquid dispenser, and a flow path from the liquid source to the liquid dispenser. A sparging device onboard the cleaner sparges the liquid by electrolysis.

DETAILED DESCRIPTION OF ILLUSTRATIVE EMBODIMENTS

Figure 1:
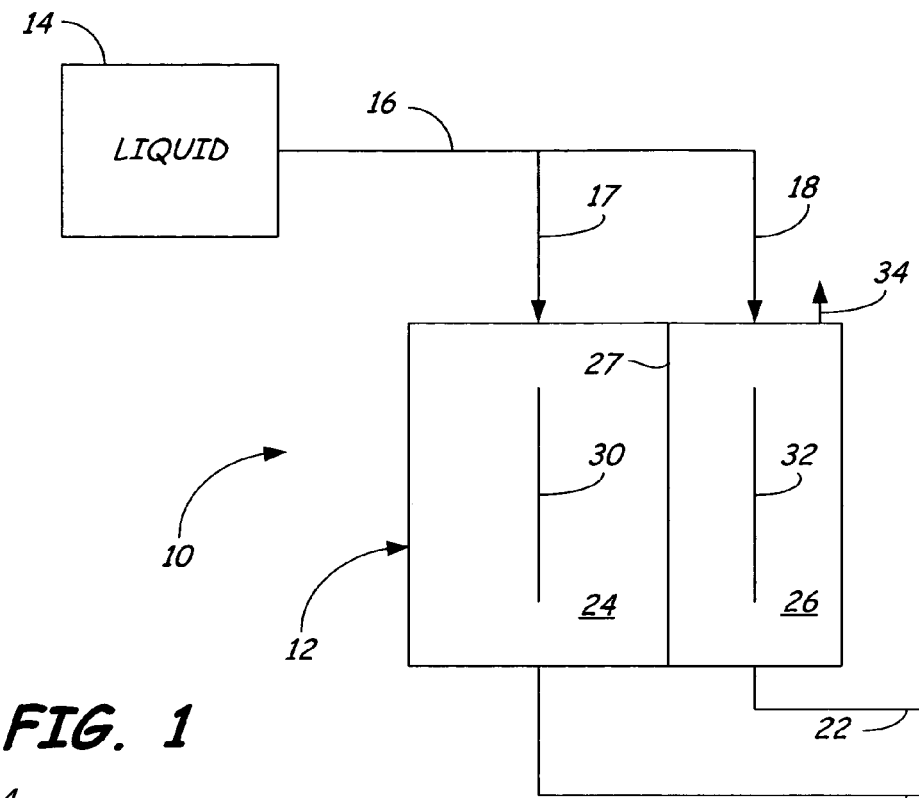
FIG. 1 illustrates an example of a functional generator, which can be used to electrochemically activate a liquid to be treated for use in cleaning, such as water, onboard or offboard a hard and/or soft floor cleaner according to an embodiment of the disclosure.

In one exemplary embodiment of the disclosure, a method and apparatus are provided, which use sparged liquid, an electrochemically activated (EA) anolyte and/or catholyte liquid, or a liquid that is both sparged and an electrochemically activated anolyte and/or catholyte liquid as the sole or primary cleaning liquid to substantially or completely eliminate the use of conventional surfactants/detergents during cleaning or disinfecting.

1. SURFACTANTS USED IN TRADITIONAL CLEANING LIQUIDS

Conventional cleaning liquids generally include water and a chemical surfactant. As used herein, the term "surfactants" or "surface-active agents" refer to amphiphilic compounds that facilitate adsorption at surfaces or interfaces as well as aggregation at certain concentrations and temperatures. The chemical make up of a surfactant adheres to a particular molecular structure. The molecule is made up of at least two components, one that is water-soluble (hydrophilic), and the other water insoluble (hydrophobic). In oil, the components are lipophilic and lipophobic respectively. The two are balanced to achieve desired properties for the surfactant.

With a cleaning apparatus that includes a mechanical scrubber, such as a mobile hard floor cleaner for example, one benefit of including surfactants has been the ability to efficiently aerate the liquid to be used in cleaning into a foam, apply the foamed cleaning liquid to the hard floor surface, work the foamed cleaning liquid with the scrub brushes, and substantially deaerate the foamed cleaning liquid prior to recovery of the soiled solution. In operation, dearation of the aerated cleaning liquid is rapidly achieved via brush contact. As a result, relatively little foam is transferred into the recovery tank.

There are basically four types of surfactants, for example—(1) anionic surfactants that dissociate into a negatively charged ion (anion) and a positively charged ion (cation) in an aqueous environment, wherein the anion becomes the carrier of the surface-active properties, (2) cationic surfactants that also dissociate into an anion and a cation, wherein the cation becomes the carrier of the surface-active properties, (3) non-ionic surfactants that are surface-active substances, which do not dissociate into ions in an aqueous environment, and (4) amphoteric surfactants that contain both a positive and a negative charge in the same surfactant molecule when present in an aqueous environment and can have anionic or cationic properties depending on the composition and conditions, such as pH value of the aqueous environment.

In general, two main tasks of the surface-active agents for cleaning include (1) reducing the surface tension of water to get wetting properties and releasing soil from surfaces, and (2) dispersing solid particles and pigment. There are many variables that come into play when it comes to producing effective cleaning surfactants and detergents. Generally, important parameters are time, temperature, aerated or non-aerated systems, concentration, soil and mechanical treatment.

2. EA LIQUIDS AND SPARGING

It has been discovered that electrochemically activated (EA) water and other EA liquids can be used with conventional cleaning systems instead of or in addition to chemical surfactant-based liquids to clean surfaces such as hard and/or soft floors. The following discussion uses EA "water" as an example of a primary cleaning liquid. However, any other suitable EA liquid or solution can be used in other embodiments.

As used herein, the term "electrochemically activated liquid" or "EA liquid" refers, for example, to water with elevated reactivity that contains (1) reactive species, and/or (2) meta-stable (activated) ions and free radicals formed after exposure to electrochemical energy in the form of a substantial voltage potential or current under non-equilibrium conditions. The term "activated" means, for example, the electrochemical or eletrophysical state or condition of having excessive inner potential energy that is attained after exposure to thermodynamically non-equilibrium conditions for a period of time. Meta-stable ions and free radicals relax in time by undergoing a gradual transition from a meta-stable state to a state of thermo-dynamic equilibrium.

As used herein, the term "electrochemical activation" refers, for example, to the process in which substances in a meta-stable state are produced during electrochemical exposure of liquid containing ions and molecules of dissolved substances to an area of special charge close to an electrode surface under non-equilibrium charge transfer conditions.

In the case of EA water production, the initial liquid source used to form EA water can include, for example, (1) regular, untreated tap water or other water that is commonly available, (2) pure water to which one or more electrolytes have been added, (3) chemically treated tap water, and (4) other aqueous solutions containing a suitable concentration of electrolytes. In one embodiment, one or more electrolytes are added to pure water (or other aqueous solution) to attain an electrolyte concentration that is greater than zero and does not exceed 0.1 moles per liter. In a further embodiment, the electrolyte concentration that is greater than zero and does not exceed 1.0 moles per liter. Other concentrations inside or outside of this range can be used in other embodiments. Examples of suitable electrolytes include chloride salt, nitrate salt, carbonate salt or any other salt that is soluble in water (or other liquid being electrochemically activated). Chloride salts include, for example, sodium chloride (such as pure NaCl), potassium chloride, magnesium chloride, calcium chloride or the like. The term "electrolyte" means any substance that dissociates into two or more ions when dissolved in water or any substance that will conduct an electric current when in solution.

EA water has enhanced cleaning power and sanitation capability when compared to non-EA water. EA water also differs from regular or untreated water at the molecular level and electron level.

It has further been discovered that a sparging device can be used to add fine gas bubbles to the EA water (or other liquid to be sparged) to create a cleaning liquid that is delivered to the surface or item to be cleaned and utilized in the cleaning process. The liquid can be sparged, for example, before or after the liquid is electrochemically activated into an anolyte and a catholyte. The resulting cleaning liquid facilitates an efficient wetting of the floor surface. If a reactive gas is used, such as oxygen, the oxygen gas bubbles can further improve the wetting properties of the liquid by reducing the surface tension of the liquid and can be reactive to further enhance the cleaning and/or sanitizing properties of the liquid.

If the liquid to be treated for use in cleaning is sparged, for example by mechanical and/or electrical methods, before being electrochemically activated, the elevated oxygen (or other gas) levels produced by sparging can assist in the electrochemical activation process to create super oxygenated EA liquid for enhanced cleaning or sanitizing power. The super oxygenated EA water contains high levels of oxygen and is electrochemically activated due to the presence of a diverse range of meta-stable ions and reactive free radicals. The end result is an electrochemically activated foam, froth or reactive gas with enhanced cleaning and/or sanitizing power.

3. FUNCTIONAL GENERATOR TO PRODUCE EA LIQUID

FIG. 1 illustrates an example of a functional generator (reactor) 10, which can be used to generate EA liquid. The terms "functional generator" and "reactor" are interchangeable herein. Functional generator 10 includes one or more electrochemical activation (EA) cells 12, which receive feed water (or other liquid to be treated for use in cleaning) from a liquid source 14 through feed lines 16, 17 and 18. Liquid source 14 can include a tank or other solution reservoir or can include a fitting or other inlet for receiving a liquid from an external source. In an embodiment, the feed water includes an aqueous composition, such as regular tap water, containing no more than 1.0 moles per liter salt. In another embodiment, the aqueous composition contains no more than 0.1 moles per liter salt. An aqueous composition containing more than 1.0 moles per liter salt can be used in further embodiments.

The term regular "tap water" means any water that is commonly available for home or commercial use, from public works, storage, wells, etc. Regular tap water typically contains salt at a concentration of less than 0.1 moles per liter. Deionized water or water in which the ionic content is negligible is less preferable since ions aid in the electrochemical activation of water. As discussed above, liquid compositions other than or in addition to regular tap water can be used as the liquid to be treated for use in cleaning and/or sanitizing and electrochemically activated for enhanced cleaning and/or sanitizing power.

Each EA cell 12 electrochemically activates the feed water by at least partially utilizing electrolysis and produces EA water in the form of an acidic anolyte composition 20 and a basic catholyte composition 22. The terms "acidic anolyte", "EA anolyte", "EA oxidized water" and "anolyte composition" are used interchangeably within the detailed description. Similarly the terms "basic catholyte", "EA reduced water," "EA catholyte" and "catholyte composition" are used interchangeably within the detailed description.

In one embodiment, each EA cell 12 has one or more anode chambers 24 and one or more cathode chambers 26 (only one shown), which are separated by an ion exchange membrane 27, such as a cation or anion exchange membrane. One or more anode electrodes 30 and cathode electrodes 32 (one of each electrode shown) are disposed in each anode chamber 24 and each cathode chamber 26, respectively. The anode and cathode electrodes 30, 32 can be made from any suitable material, such as titanium or titanium coated with a precious metal, such as platinum, or any other suitable electrode material. The electrodes and respective chambers can have any suitable shape and construction. For example, the electrodes can be flat plates, coaxial plates, rods, or a combination thereof. Each electrode can have, for example, a solid construction or can have one or more apertures, such as a metallic mesh. In addition, multiple cells 12 can be coupled in series or in parallel with one another, for example.

The electrodes 30, 32 are electrically connected to opposite terminals of a conventional power supply (not shown). Ion exchange membrane 27 is located between electrodes 30 and 32. The power supply can provide a constant DC output voltage, a pulsed or otherwise modulated DC output voltage, or a pulsed or otherwise modulated AC output voltage to the anode and cathode electrodes. The power supply can have any suitable output voltage level, current level, duty cycle or waveform.

For example in one embodiment, the power supply applies the voltage supplied to the plates at a relative steady state. The power supply includes a DC/DC converter that uses a pulsewidth modulation (PWM) control scheme to control voltage and current output. The DC/DC converter uses approximately a 15 kHz pulse to produce the desired voltage to the anode and cathode in the range of 5V to 25V, such as a voltage of 15V with a power up to about 120-150 Watts. The duty cycle is dependent on desired voltage and current output. For example, the duty cycle of the DC/DC converter can be 90%. As explained in more detail below, the power supply can be configured, if desired, to alternate between a relative steady state voltage for 5 seconds at one polarity and then a relative steady state voltage for 5 seconds at the opposite polarity.

Other types of power supplies can also be used, which can be pulsed or not pulsed and at other voltage and power ranges. The parameters are application-specific.

Feed water is supplied from source 14 to both anode chamber 24 and cathode chamber 26 via feed water supply line 16, which can be branched into anode supply line or manifold 17 and cathode supply line or manifold 18. The anode supply line 17 supplies the feed water to each anode chamber 24, and the cathode supply line 18 supplies the feed water to each cathode chamber.

In the case of a cation exchange membrane, upon application of a DC voltage potential across anode 30 and cathode 32, such as a voltage in a range of about 5 Volts (V) to about 25V, cations originally present in the anode chamber 24 move across the ion-exchange membrane 27 towards cathode 32 while anions in anode chamber 24 move towards anode 30. Similarly, cations present in the cathode chamber 26 move towards cathode 32. However, anions present in cathode chamber 26 are not able to pass through the cation-exchange membrane, and therefore remain confined within cathode chamber 26.

In addition, water molecules in contact with anode 30 are electrochemically oxidized to oxygen ($O_2$) and hydrogen ions ($H^+$) in the anode chamber 24 while water molecules in contact with the cathode 32 are electrochemically reduced to hydrogen gas ($H_2$) and hydroxyl ions ($OH^-$) in the cathode chamber 26. The hydrogen ions in the anode chamber 24 are allowed to pass through the cation-exchange membrane 27 into the cathode chamber 26 where the hydrogen ions are reduced to hydrogen gas while the oxygen gas in the anode chamber 24 oxygenates the feed water to form the anolyte 20. Furthermore, since regular tap water typically includes sodium chloride and/or other chlorides, the anode 30 oxidizes the chlorides present to form chlorine gas. As a result, a substantial amount of chlorine is produced and the pH of the anolyte composition 20 becomes increasingly acidic over time.

As noted, water molecules in contact with the cathode 32 are electrochemically reduced to hydrogen gas and hydroxyl ions ($OH^-$) while cations in the anode chamber 24 pass through the cation-exchange membrane 27 into the cathode 32 when the voltage potential is applied. These cations are available to ionically associate with the hydroxyl ions produced at the cathode 32, while hydrogen gas typically bubbles to the surface and escapes the cathode chamber 26, as noted by arrow 34. As a result, a substantial amount of hydroxyl ions accumulates over time in the cathode chamber 26 and reacts with cations to form basic hydroxides. In addition, the hydroxides remain confined to the cathode chamber 26 since the cation-exchange membrane does not allow the negatively charged hydroxyl ions pass through the cation-exchange membrane. Consequently, a substantial amount of hydroxides is produced in the cathode chamber 26, and the pH of the catholyte composition 22 becomes increasingly alkaline over time.

Since hydrogen gas 34 readily escapes from the cathode chamber 26, the electrochemical reactions of the functional generator 10 never reach equilibrium. As a result, the non-equilibrium conditions of the electrolysis process in the functional generator 10 allow concentration of reactive species and the formation of metastable ions and radicals in the anode chamber 24 and cathode chamber 26 chamber.

The electrochemical activation process typically occurs by either electron withdrawal (at anode 30) or electron introduction (at cathode 32), which leads to alteration of physiochemical (including structural, energetic and catalytic) properties of the feed water. It is believed that the feed water (anolyte or catholyte) gets activated in the immediate proximity of the electrode surface where the electric field intensity can reach a very high level. This area can be referred to as an electric double layer (EDL).

Alternatively, for example, an aqueous composition containing deionized water and up to 0.1 moles per liter salt, such as 0.1 moles per liter sodium chloride, can be introduced into the anode and cathode chambers 24 and 26. The sodium chloride fully dissociates into positively charged sodium ions ($Na^+$) and negatively charged chloride ions ($Cl^-$). The sodium and chloride ions become hydrated by water molecules. Positively charged sodium ions present in the water move towards cathode 32 while negative chloride ions move towards anode 30.

Water is oxidized to oxygen gas and hydrogen ions at anode 30 and reduced to hydroxyl ions and hydrogen gas at cathode 32. Sodium ions located near or on the surface of the cathode 32 are therefore capable of ionically associating with the negatively charged hydroxyl ions to form sodium hydroxide. As a result, cathode chamber 26 contains water and hydroxides, which cause an increase in the pH, and the water becomes increasingly alkaline over time.

Similarly, chloride ions present in anode chamber 24 become electrochemically oxidized to chlorine gas. Hydrogen ions or other cations present in anode chamber 32 are transferred through cation-exchange membrane 27. As a result, anode chamber 24 contains chlorine and oxygen gas that cause a decrease in pH over time.

As mentioned, hydrogen gas readily escapes from aqueous compositions; hence, the electrochemical reactions do not reach equilibrium. As a result, the non-equilibrium condition of the electrolysis process in the functional generator 10 continues to allow concentration of reactive species and the formation of metastable ions and radicals in the anode chamber 24 and cathode chamber 26.

In another embodiment, one or both of electrodes 30 and 32 can be coated with silver. Alternatively, for example, additional electrodes can be added to chamber 12, which are coated or embedded with silver. The silver slowly dissolves during use, thereby releasing silver ions, such as silver nano-ions, into the anolyte and/or catholyte. The silver ions can help increase the sanitizing properties of the produced EA liquid.

4. ION EXCHANGE MEMBRANE

As mentioned above, the ion exchange membrane 27 can include a cation exchange membrane or an anion exchange membrane. In the case of a cation exchange membrane, the membrane may be in the form of a single-layer membrane derived from one perfluoroionomer resin, for example. Alternatively, for example, the cation-exchange membrane 27 may be in the form of a two-layer membrane derived from the same or two different perfluoroionomer resins, for example. Other materials can also be used having various numbers of layers. In addition, membranes are usually reinforced by a porous structure or body that is made of polytetrafluoroethylene (PTFE), for example, to provide sufficient mechanical strength.

Cation-exchange membranes include anion-exchange groups ($-SO_3^-$ or $-COO^-$), for example, which are covalently bound to the polymer skeleton. During operation, ionic salts disassociate in water into cations or anions. The cations are referred to as counter ions while anions are referred to as co-ions of the cation-exchange membrane.

Under an electrical potential gradient existing in electrochemical cell, $Na^+$ and $H^+$ ions clustering with water molecules are transported through the membrane toward the negative charged cathode and co-ions ($Cl^-$ and $OH^-$) are transported toward positively charged anode.

Even though cation-exchange membranes selectively transmit $Na^+$, other cations and water molecules but suppress diffusion of $Cl^-$ and $OH^-$ ions, some hydroxyl anions are still able to migrate through the cation-exchange membrane. The main net result is an enrichment of $Cl^-$ ions in anode chamber 24 and $Na^+$ (and to a lesser degree $H^+$) ions in cathode chamber 26, and extremely low diffusion of $Cl^-$ anions from anolyte 20 to catholyte 22 and $OH^-$ anions from catholyte 22 to anolyte 20. In one embodiment, to limit or prevent hydroxyl ion migration, the side of the perfluorosulfonic acid membrane contacting the catholyte 22 can be covered by a layer of perfluorocarbohylyc acid polymer.

The charge of bonded ions in the cation-exchange membrane is balanced by equivalent charges of counter ions in the form of $H^+$, $Li^+$, $Na^+$, $K^+$, and the like. Cation-exchange membranes typically work when sufficiently hydrated. When a polymer is placed in water, the polymer swells, becomes pliable and allows ions to move freely under the action of a voltage potential or by diffusion. As a result, it is believed the cation-exchange membrane behaves like an ion conductor in an electric field and can transmit cations with high selectivity.

It is also believed the hydrogen ($R-SO_3H$) and sodium ($R-SO_3Na$) forms of strong acid resins are highly dissociated and the exchangeable $Na^+$ and $H^+$ are readily available for exchange over the entire pH range. Hence, exchange capacity and therefore process efficiency is not pH dependent. However, it is believed hydrogen ($R-COOH$) and sodium ($R-COONa$) forms of weak carboxylic acids the dissociation is not high and is very pH dependent. Consequently, the exchange capacity of weak carboxylic acids is strongly pH dependent as is the process efficiency when such membranes are employed.

The operation of cation-exchange membranes is also a function of (1) ionic conductivity or the total transport of cations through the membrane, (2) ion current density, (3) ion transport number or the current carried by a specific ion relative to the total current applied, (4) molecular weight of the backbone polymer, (5) porosity of the membrane, (6) equivalent weight or weight of dry polymer in grams containing one mole of sulfonic acid group, (7) ion exchange capacity or total number of chemical equivalent of sulfonic acid groups available for exchange per unit weight or unit volume of polymer resin, (8) hydration or percent water adsorbed by the polymer and/or (9) water transport.

Examples of suitable cation-exchange membranes that can be used in functional generator 10 include Nafion membranes from DuPont, USA, Flemion membranes from Asahi Glass Co., Japan, Aciplex membranes from Asahi Chemical Industries Co., Japan and Dow membranes from Dow Chemical, USA. An example of a suitable functional generator includes the Emco Tech "JP102" cell found within the JP2000 ALK-ABLUE LX, which is available from Emco Tech Co., LTD, of Yeupdong, Goyang-City, Kyungki-Do, South Korea. This particular cell has a DC range of 27 Volts, a pH range of about 10 to about 5.0, a cell size of 62 mm by 109 mm by 0.5 mm, and five electrode plates. Other types of functional generators can also be used, which can have various different specifications.

5. PROPERTIES OF THE EA WATER OUTPUT

Electrochemical activation within functional generator 10 produces EA water that can be used for cleaning and/or sanitizing. The EA water is produced in the form of an acidic anolyte 20 and a basic catholyte 22 at the outputs of anode chamber 24 and cathode chamber 26, respectively.

A. Anolyte

Anolyte 20 is acidic in nature and contains very strong oxidants in the form of active chlorine ($Cl_2$), for example. In one embodiment, anolyte 20 has a pH of about 2.0 to about 4.0, but can have a pH outside of that range in other embodiments, such as in a range of about 2.5 to 6. In one embodiment, anolyte 20 has an oxidation-reduction potential (ORP) of about +600 mV to about +1200 mV, or can be in other ranges such as +100 mV to +1200 mV, +400 mV to +900 mV, or +400 mV to +700 mV, for example. Other values of pH, oxidation-reduction potential and chlorine concentration can be used in other embodiments. Intensity of oxidation-reduction reactions depends on electron activity in aqueous solutions, which is characterized by the oxidation-reduction potential (ORP) value. The higher the ORP value, the more "acid" the medium, and the more it is capable of oxidating molecules. The lower ORP value, the higher its reducing, anti-oxidant, ability. As a result of electrochemical exposure of water near the anode, its oxidation-reduction potential increases, and it acquires oxidant characteristics.

Anolyte 20 can be used wherever there is a desire to disinfect or sterilize. Anolyte 20 can be used to kill bacteria since water having this range of oxidation-reduction potential changes the environment in which microbes, viruses, germs and other biological life forms can thrive and attracts electrons from the environment and microbes. As a result, the environment and microbes are oxidized. Therefore, EA anolyte water can be used as a disinfectant and sanitizer during operation of a surface cleaner in one or more embodiments. However, care should be taken on surfaces having a potential for corrosion.

Anolyte 20 may also contain many meta-stable ionic and reactive free radical molecules produced at the anode 30 during electrochemical activation of water. These molecules can include: $O_3$, $O_2$, $H_2O_2$, $Cl_2$, $ClO_2$, $HClO$, $HCl$, $HClO_3$, $O_2^-$, $H_2O_2$, $O_3$, $H^+$, $H_3O^+$, $OH^-$, $ClO^-$, $HO^{\bullet}$, $H_2O^{\bullet}$, $O_2^{\bullet}$, $O^{\bullet}$, $ClO^{\bullet}$, and $Cl^{\bullet}$ free radicals and other excited molecules.

Molecular chlorine can also react to form hypochlorous acid and other ions of $OCl^-$ ions. These ions of OCl— can further oxidize and become chloric acid ions ($ClO_3^-$) and perchloric acid ion ($HClO_4^-$). Chlorine dioxide may also be obtained by oxidation of sodium chloride and hydrochloric acid. Furthermore, many other pH-dependent reactions result in a wide variety of very meta-stable and/or reactive chlorine containing molecules, ions and free radicals. In addition to the sanitizing properties, the chlorine ions in the mildly acidic anolyte solution 20 can react with metal oxides in scale deposits on the surface being cleaned, which assist in removing the scale deposits.

B. Catholyte

As a result of electrochemical exposure of water near the cathode, its oxidation-reduction potential decreases, and it acquires anti-oxidant characteristics. Catholyte 22 is strongly basic, and the pH of the catholyte solution ranges from about 8 to about 12, or from 9 to about 12 in one or more embodiments. However, the catholyte can have pH values outside of this range in other embodiments. In one embodiment, catholyte 22 has an ORP of about −600 mV to about −1000 mV, or the ORP can be in other ranges such as −150 mV to −1000 mV, −150 mV to −700 mV, or −300 mV to −700 mV. Catholyte 22 can be used for flocculation of heavy metals, coagulation, washing, and extraction. In addition, catholyte 22 can be used to wash wounds (instead of using iodine) and wherever there is a need to increase pH levels of water. Catholyte 22 may also include reactive hydrogen peroxide ($H_2O_2$), sodium and other hydroxides, meta-stable ions, and/or free radicals.

Water molecules cluster typically together at 12-14 molecules per cluster around ions, for example. This is sometimes known as "Surface Tension". Normal tap water includes a network of icosahedral water clusters. These large water conglomerates are too large to easily penetrate different organic and inorganic materials and biological objects, which can be a time-consuming and energy consuming process. The degradation of large water clusters into smaller clusters can make water more active and more valuable for practical applications. When the functional generator electrochemically activates water, the covalent hydrogen bonds between hydrogen and oxygen is broken resulting in the clusters of $H_2O$ being reduced to below 10 molecules per cluster, such as between 5 and 6 molecules per cluster. The resulting EA water therefore has a distribution of water cluster sizes that has a greater number of smaller-sized clusters. The EA water is therefore much "wetter" has more wetting ability, more permeable, and more soluble. Because EA water is wetter has more wetting ability than typical water, it can hydrate six to ten times (for example) faster than non-EA water and will act as a transport mechanism for lifting and separating debris from the surface being cleaned more readily than non-EA water.

More specifically, EA water in the form of the basic catholyte composition has the capacity to mimic anionic, cationic, nonionic and amphoteric surfactants. Catholyte 22 has a surfactant mimicking effect since the catholyte 22 can have a high pH and is packed with a very large quantity of negative ions after electrochemical activation. In one embodiment, catholyte 22 is highly alkaline with a pH of 9 or greater, for example in the range of about 10 to about 12, but can have other pH values outside of this range in other embodiments. Water molecule clusters typically surround ions when in solution. During electrochemical activation, electrons and ions furiously move about within water molecule clusters and bombard each other until the water molecule cluster becomes very small. Consequently, these smaller water molecule clusters are able to penetrate cracks and crevices between dirt and objects, and are able to lift dirt more effectively than ordinary non-EA water.

Catholyte 22 is able to enhance dispersion in a manner similar to that observed when using commonly known surfactants. These effects are observed since catholyte 22 contains negative ions that envelope any molecules of objects and dirt. Enveloping or surrounding molecules of objects and dirt with negative charges creates a negative potential that causes molecules of objects and dirt to repel each other and remain separate.

These properties also improve solvation and removal of grease, acidic soils, and carbonaceous oils. This is because catholyte 22 surrounds grease molecules with negative charges that can be lifted off separately after being surrounded by negative ions. In addition, surrounding grease molecules with negative charges helps to reduce the overall size of grease molecules, and therefore catholyte 22 causes grease molecules to become smaller.

Furthermore, surrounding grease molecules with negative charges effectively saponifies the grease molecules and helps emulsify or stabilize hydrophobic grease molecules in water. When a fatty or grease like substance is surrounded by negative charges from catholyte 22, catholyte transforms grease into a synthetic liquid soap. As a result, oily or greasy stains become soluble and can be removed by catholyte 22 without addition of surfactant/detergent chemistry as part of the cleaning liquid. However, a surfactant/detergent can be added to the liquid to be treated for use in cleaning before or after activation, if desired, in other embodiments.

Catholyte 22 therefore has strong cleaning capacity. Catholyte 22 can be used as a cleaning solution with a high level of cleaning power, is safe and does not pollute the environment. Catholyte 22 is safe to the environment since reduced water reduces matter and does not oxidize matter. Oxidization causes some materials to rust, degrade, age and become dirty. Catholyte 22 avoids rusting, degradation, premature aging and dirtying.

The EA water (catholyte and anolyte) produced from functional generator 10 therefore has cleaning power and bacteria-killing power. As a result, a cleaning apparatus, such as a mobile or immobile hard and/or soft floor cleaner, can use EA water to clean floors and other off-floor surfaces of industrial, commercial and residential buildings, for example. The cleaner can use the EA water without the addition of surface-active ingredients, such as a surfactant or detergent to aid in the cleaning of hard and/or soft surfaces.

Also, the EA water produced by functional generator 10 has a solvating power that is very effective in forcing oils into a solution that can be extracted from the surface. In contrast to detergents that tend to keep oils in suspension, EA water allows oils to recombine after extraction when the water loses its activated properties and neutralizes. When used with a cleaning apparatus that has a soiled-liquid recovery function, this characteristic of the EA water allows oils to be separated from the extracted, soiled water more efficiently. This may reduce the expenses associated with disposing of the soiled wastewater recovered from the surface or item being cleaned.

As described in more detail below, the anolyte and catholyte can be separately applied to and extracted from the surface or item being cleaned or can be applied together, either sequentially or as a mixture. The anolyte and catholyte can be applied through separate distribution systems or can share the same distribution system. In one example, if a particular one of the anolyte and catholyte is not used, it can be routed from the output of functional generator to a buffer or reservoir for later use or can be routed to a waste or recovery tank. The terms tank, buffer, and reservoir are interchangeable.

C. Blended Anolyte and Catholyte

It has been found that the anolyte and catholyte can be blended together within the distribution system of the cleaning apparatus and/or on the surface or item being cleaned while still retaining beneficial cleaning and sanitizing properties. A blended EA water composition may also be formed by blending varying ratios of anolyte 20 and catholyte 22 with each other. Upon blending, the blended EA water is in a non-equilibrium state and may include anolyte species having a pH of about 2.5-6 and an ORP of −150 mV to −700 mV, for example, and catholyte species having a pH of about 8-12 and an ORP of about +400 mV to about +900 mV, for example. It is believed that the small water clusters do not allow the reactive species in the anolyte and catholyte to recombine and neutralize instantaneously. Although the anolyte and catholyte are blended, they are initially not in equilibrium and therefore temporarily retain their enhanced cleaning and sanitizing properties.

Also for a typical mobile surface cleaner or for an extractor type of cleaner, the residence time of the liquid on the surface being cleaned before extraction is relatively short, such as between 2-3 seconds for a typical mobile surface cleaner. This allows the oxidation-reduction potential and other beneficial cleaning/sanitizing properties of a blended EA water to be substantially retained during the residence time before these properties substantially neutralize in the recovery tank of the cleaner or following disposal.

6. VARYING PRODUCTION CONCENTRATIONS AND VOLUMES OF ANOLYTE AND CATHOLYTE

The anolyte and catholyte can be generated or applied in different ratios to one another through modifications to the structure of the functional generator 10, the flow rates through the generator and/or the distribution system.

For example, the functional generator can be configured to produce a greater volume of catholyte than anolyte if the primary function of the EA water is cleaning. Alternatively, for example, the functional generator can be configured to produce a greater volume of anolyte than catholyte if the primary function of the EA water is sanitizing. Also, the concentrations of reactive species in each can be varied.

Figure 2:
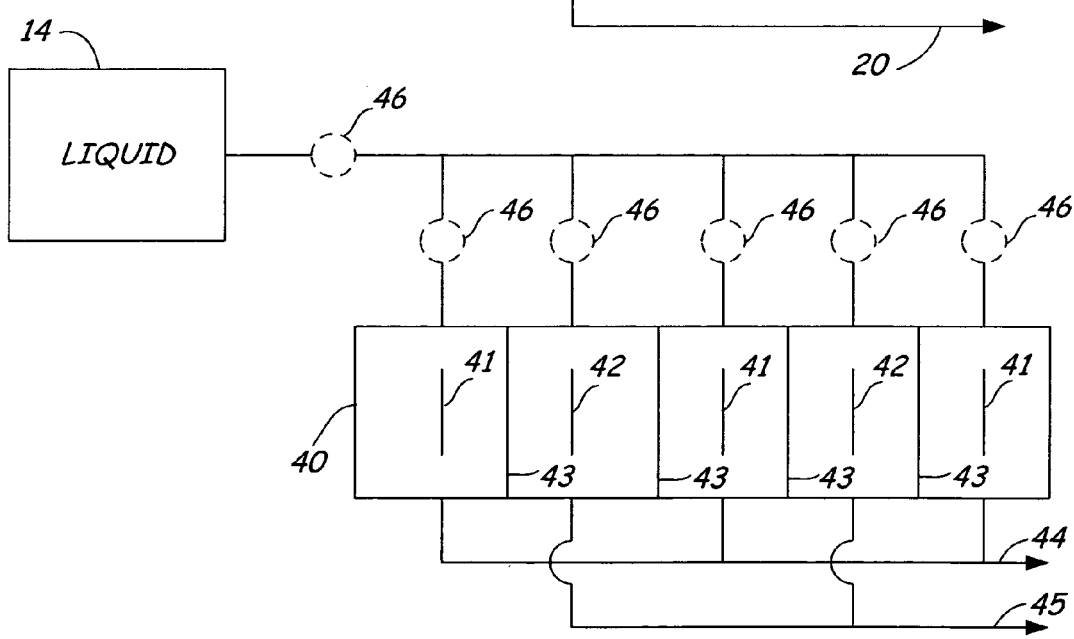
FIG. 2 illustrates a functional generator according to another embodiment of the disclosure.

FIG. 2 illustrates a schematic diagram of a functional generator 40 according to an embodiment having a 3:2 ratio of cathode plates 41 to anode plates 42 for producing a greater volume of catholyte than anolyte. Each cathode plate 41 is separated from anode plate 42 by a respective ion exchange membrane 43. Thus, there are three cathode chambers for two anode chambers. This configuration produces roughly 60% catholyte through output 44 to 40% anolyte through output 45. In another embodiment, each cell includes three cathode chambers and one anode chamber, each being separated by a respective membrane, similar to the embodiment shown in FIG. 2. Other ratios can also be used.

With multiple anode and cathode chambers, the ratios can be further modified by electrically enabling and disabling selected electrode plates. Enabling and disabling can be achieved with suitable switches in the power supply lines to the electrodes, which can be controlled automatically by a control circuit, manually by an operator or a combination of both. In the example shown in FIG. 2, a 1:1 ratio can be achieved by disabling one of the cathodes 41 and cutting flow to that chamber. A 2:3 ratio of cathode plates to anode plates can be achieved in this example by simply reversing the polarity of the electrical potential applied to plates 41 and 42. Thus, each plate 41 becomes an anode plate, while each plate 42 becomes a cathode plate. The polarity of the applied voltage can also be reversed periodically or at other times to self-clean the anode and cathode plates and therefore extend their life. Therefore, the terms "anode" and "cathode" and the terms "anolyte" and "catholyte" as used in the description and claims are respectively interchangeable.

Alternatively or in addition, flow to selected chambers can be mechanically enabled, disabled or reduced through flow restriction devices 46, which can be positioned at the input end or output end of functional generator 40. Flow restriction devices can include any device that is adapted to restrict flow, such as a valve or pump.

The concentration of reactive species, change in pH or reduction potential in each chamber can be adjusted by adjusting the flow through that chamber. With a higher flow rate in a particular chamber, the feed water has a shorter residence time in the chamber and thus less time to generate reactive species or change pH or reduction potential.

Functional generator 40 can also have multiple cells in parallel with one another, which can be selectively enabled and disabled as desired.

In another embodiment one or more of the cathode plates can have a different surface area than a respective anode plate to alter the concentration of active water produced in one chamber relative to another.

In another embodiment of the disclosure, catholyte output 44 and anolyte output 45 are combined in the flow path at the output of functional generator 40.

7. SPARGING

Figure 3:
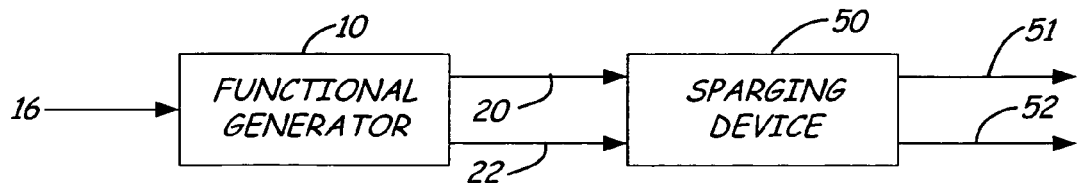
FIG. 3 illustrates an apparatus having a sparging device located downstream of a functional generator, according to an embodiment of the disclosure.

As mentioned above, it has been found that sparging the liquid to be treated for use in cleaning downstream or upstream of the functional generator can enhance the cleaning or sanitizing properties of the resulting liquid. Alternatively, for example, a sparging device can be used by itself, with no functional generator, in any apparatus, such as but not limited to those disclosed herein. In one embodiment, the term "sparging" means to disperse a gas in a liquid or to disperse a liquid in a gas by any appropriate method as will be appreciated by those of ordinary skill in the art. The terms "sparged EA liquid" and "sparged EA water" refers to EA liquid or EA water that has been sparged upstream and/or downstream of the functional generator that electrochemically activates the liquid or water. FIG. 3 illustrates an apparatus having a sparging device 50 located downstream of functional generator 10. Sparging device 50 sparges or infuses anolyte EA liquid 20 and catholyte EA liquid 22 with a gas to form sparged anolyte EA liquid 51 and sparged catholyte EA liquid 52. A single, combined sparging device or separate devices can be used to sparge each of the flow streams. Alternatively, for example, sparging device 50 is coupled to sparge only one or the other of the anolyte EA liquid 20 and the catholyte EA liquid 22. In a further embodiment, for example, the flow streams 20 and 22 are combined to a single stream before being sparged by device 50. Also, multiple sparging devices can be coupled together in series for in parallel with one another, for example.

In one embodiment, sparging device 50 disperses fine gas bubbles to the EA liquid to create a froth that is delivered to the surface or item to be cleaned. Suitable gases include air, oxygen, nitrogen, ammonia, carbon dioxide and other gases. In the cases of air and oxygen, the resulting sparged EA liquid becomes highly oxygenated. The increase in oxygenation further facilitates an efficient wetting of the surface or item being cleaned and can enhance chemical reactions that facilitate cleaning or sanitizing.

Sparging device 50 may include a variety of froth generation devices, including but not limited to devices that operate on a mechanical basis, devices that operate on an electrochemical basis, such as by electrolysis, and devices that operate on a chemical basis, or a combinations thereof. Mechanical sparging devices can be adapted to disperse a gas in the liquid or disperse the liquid in a gas. Examples include pressurized or non-pressurized gas delivery systems, pressurized or non-pressurized liquid delivery systems, agitation systems, sprayers, and bubblers. In one embodiment, a pressurized gas is introduced into the flow path of the liquid being treated for use in cleaning and then dispersed in the liquid by a suitable mixing member, such as a diffusion medium that is capable of producing froth by shearing action, gas entrainment or a combination of both. In another embodiment, a Venturi tube can be used to introduce a gas into the liquid flow path, for example.

Figure 4:
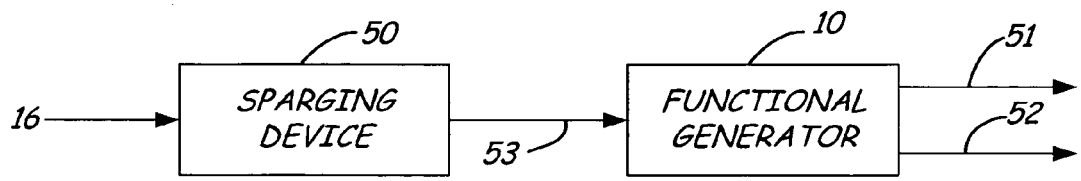
FIG. 4 illustrates an apparatus having a sparging device located upstream of a functional generator, according to an embodiment of the disclosure.

If sparging device 50 is placed upstream of functional generator 10, such as in the embodiment shown in FIG. 4, the gas can also assist in the electrochemical activation process to enhance the cleaning or sanitizing power of the resulting EA liquid. The sparged liquid 53 from sparging device can be supplied to the anode chamber, the cathode chamber or both the anode and cathode chambers of functional generator 10, while regular tap water (or other liquid) can be supplied to any chamber not receiving the sparged liquid.

If the sparged gas includes air or oxygen, the elevated oxygen levels during electrochemical activation can create super oxygenated EA water. The increased levels of oxygen increase efficiency of the electrochemical activation process. Also, during the electrochemical activation process, the sparged water may have a distribution of water cluster sizes that has a greater number of smaller clusters having lower numbers of water molecules per cluster. These smaller clusters may increase efficiency in transport and separation through the ion exchange membrane of the functional generator. The super oxygenated EA water becomes electrochemically activated, resulting in an electrochemically activated foam, froth, and/or reactive gas with enhanced cleaning or sanitizing power.

Figure 5:
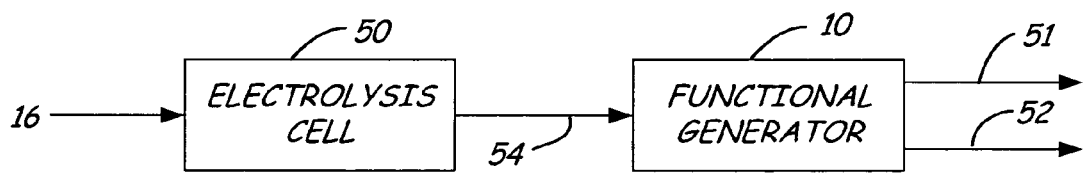
FIG. 5 illustrates an apparatus having an electrolysis cell type sparging device located upstream of a functional generator, according to an embodiment of the disclosure.

In the embodiment shown in FIG. 5, sparging device 50 includes one or more electrolysis cells that operate on an electrochemical basis to accomplish sparging. The electrolysis cells can be positioned upstream or downstream of the functional generator 10. In FIG. 5, an electrolysis cell 50 is upstream of functional generator 10. The electrolysis cell has one or more anodes and one or more cathodes similar to the functional generators shown in FIGS. 1 and 2. However in one embodiment, the electrolysis cell has no ion exchange membrane.

In addition, sparging device 50 can be positioned along the flow path from liquid source 14 (shown in FIGS. 1 and 2) or inside of the liquid source 14, such as in a source tank carried by a mobile floor surface cleaner.

Regular tap water typically contains 8 to 40 mg/L of oxygen. Oxygen levels can be boosted by electrolysis. Electrolysis of the feed water from the water source (or of the EA water from functional generator 10) can introduce oxygen gas and hydrogen peroxide into the water. The oxygen and other gas bubbles not only further improve the wetting properties of the water by reducing the surface tension of the water, these gas bubbles can also be reactive to further enhance the cleaning and/or sanitizing properties of the water. The oxygenated water 54 produced by electrolysis may also contain hydrogen peroxide, which is a strong oxidizer and can further boost the sanitizing properties of the water.

Sparging may result in the introduction of "micro-bubbles" or "nano-bubbles". Micro-bubbles and nano-bubbles have a size that is generally too small to break the surface tension of the liquid. As a result these bubbles remain suspended indefinitely in the liquid. Indefinite suspension of bubbles allows for increased concentration of bubbles, and ultimately, super-saturation of water with the gas bubbles.

Figure 6:
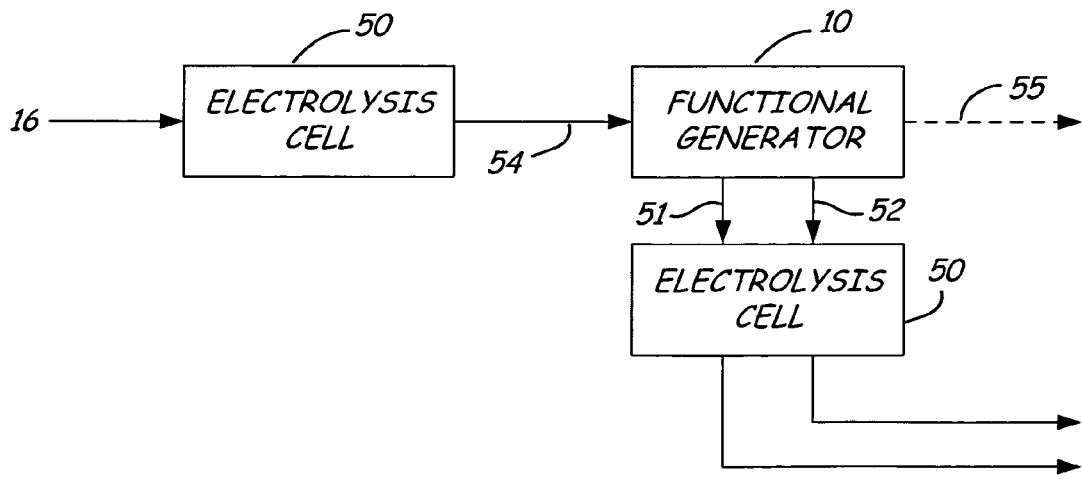
FIG. 6 illustrates an apparatus having sparging devices located upstream and downstream of a functional generator, according to an embodiment of the disclosure.

FIG. 6 is a diagram illustrating an embodiment similar to that of FIG. 5, but further including a second electrolysis cell (or other device to accomplish sparging) 50 downstream of functional generator 10 for additional electrolysis and oxygen generation to produce a reactive froth with superior cleaning or sanitizing capacity. In one embodiment, the super-oxygenated anolyte and catholyte outputs from functional generator 10, represented by arrows 51 and 52, are passed through the second electrolysis cell 50, either separately through two separate chambers or mixed together. In another embodiment, one of the outputs, such as the super-oxygenated anolyte output, is passed through the second cell 50 while the other output, such as super-oxygenated catholyte output, bypasses the second cell 50, as shown by arrow 55. By electrochemically activating water prior to electrolysis by the additional cell 50, less electrical resistance may be encountered during the electrolysis process used to sparge the liquid. In addition, more effective retention of the nano-bubbles in the final reactive froth may be attained.

In a further embodiment, a tank can be filled from a previously-sealed container of EA liquid or can be filled from a nearby stationary or mobile "filling station", which carries a functional generator for electrochemically activating a liquid and then loading the tank through a hose or other temporary attachment to the cleaner. After loading the EA water, the EA water is delivered to a sparging device before delivery to the surface or item to be cleaned or sanitized.

In yet a further embodiment, a tank can be filled from a previously-sealed container of sparged liquid or can be filled from a nearby stationary or mobile "filling station", which carries a sparging device for sparging a liquid and then loading the tank through a hose or other temporary attachment to the cleaner. After loading the sparged liquid, the liquid is delivered to a functional generator for electrochemical activation before delivery to the surface or item to be cleaned or sanitized. In one example, a sparged liquid is contained in a container having a suitable internal pressure to maintain the sparged state of the liquid until delivery or use. The container can be emptied into a tank carried by the cleaning device and/or can be configured to be connected directly into the flow path of the device, either upstream or downstream of the functional generator.

8. ELECTROLYSIS CELL

Figure 7:
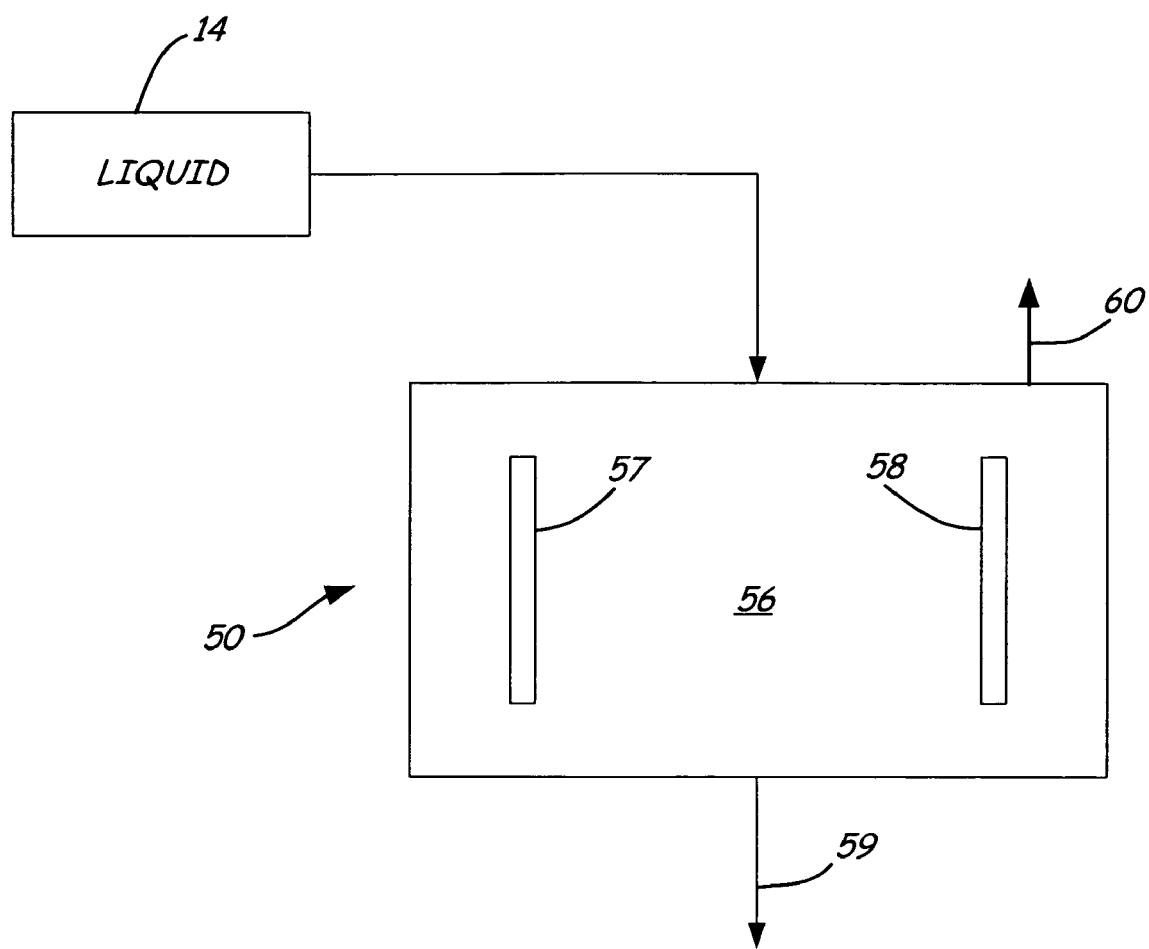
FIG. 7 illustrates an electrolysis cell type sparging device, according to an embodiment of the disclosure.

FIG. 7 is a block diagram of an electrolysis cell 50 that can be used as a sparging device according to one embodiment of the present disclosure. Cell 50 includes a reaction chamber 56, an anode 57 and a cathode 58. Chamber 56 can be defined by the walls of cell 50, by the walls of a container or conduit in which electrodes 57 and 58 are placed, or by the electrodes themselves, for example. Anode 57 and cathode 58 may be made from any suitable material or a combination of materials, such as titanium or titanium coated with a precious metal, such as platinum. Anode 57 and cathode 58 are connected to a conventional electrical power supply (not shown). In one embodiment, electrolytic cell 50 includes its own container that defines chamber 56 and is located in the flow path of the liquid to be treated in the cleaning apparatus. In another embodiment, electrolysis cell 50 includes anode 57 and cathode 58 but no container. In these embodiments, the reaction chamber 56 may be defined by a container or conduit section in which the electrodes are placed.

In another example, the anode and cathode electrodes can be placed inside liquid tank 14, shown in FIGS. 1 and 2.

In a further example, the anode and cathode electrodes can be placed inside or along a section of conduit positioned along the liquid flow path of the cleaning apparatus.

Electrolysis cell 50 and its electrodes can have any physical shape and construction. For example, the electrodes can be flat plates, coaxial plates, rods, or a combination thereof. Each electrode can have a solid construction or can have one or more apertures, such as a metallic mesh.

During operation liquid is supplied by a source 14, such as tank 14 in FIGS. 1 and 2 and/or functional generator 10, and is introduced into electrolysis chamber 56 of electrolysis cell 50. In the embodiment shown in FIG. 7, electrolysis cell 50 does not include an ion exchange membrane that separates reaction products at anode 57 from reaction products at cathode 58. In the example in which tap water is used as the liquid to be treated for use in cleaning, after introducing the water into chamber 56 and applying a voltage potential between anode 57 and cathode 58, water molecules in contact with or near anode 57 are electrochemically oxidized to oxygen ($O_2$) and hydrogen ions ($H^+$) while water molecules in contact or near cathode 58 are electrochemically reduced to hydrogen gas ($H_2$) and hydroxyl ions ($OH^-$). The reaction products from both electrodes are able to mix and form an oxygenated fluid 59 having a neutral pH and an ORP in the range of about 500 mV to about 800 mV since there is no physical barrier separating the reaction products from each other. Hydrogen gas 60 typically bubbles to the surface of the fluid surrounding the cathode 58 and escapes into the atmosphere air while oxygen gas remains suspended in water for longer periods of time since oxygen gas is much denser than hydrogen gas. As a result, fluid 59 becomes supersaturated with oxygen and has a strong ORP. If electrolysis cell 50 is placed upstream of the functional generator, the super-oxygenated, strong ORP, and reduced cluster size properties of the incoming fluid can greatly assist the electrochemical activation process within the functional generator.

Alternatively, for example, anode 57 can be separated from cathode 58 by using a dielectric barrier such as a non-permeable membrane (not shown) disposed between the anode and cathode.

9. SPARGING ENHANCES BLENDED ANOLYTE AND CATHOLYTE EA WATER

It has also been found that sparging upstream and/or downstream of the functional generator can also enhance and help retain the cleaning and/or sanitizing properties of the water when anolyte EA water is blended with catholyte EA water.

A simple experiment was performed in which various types of EA water were placed in an open container and a drop of oil was placed on the water surface to measure the oil dispersion properties of each EA water type. Non-sparged anolyte EA water showed no oil dispersing properties. Non-sparged and sparged catholyte EA water showed 100% oil dispersing properties, wherein the oil was dispersed over 100% of the water surface. Non-sparged anolyte and catholyte EA water, when combined, showed 100% oil dispersion. Sparged anolyte EA water showed 50% oil dispersing properties, wherein the oil was dispersed over 50% of the water surface, as compared to 0% for the non-sparged anolyte EA water. The sparged anolyte and catholyte EA water, when combined, showed 100% oil dispersion.

The 50% increase in oil dispersion properties for the sparged anolyte suggests that the blended EA water has increased oil dispersion capability, which should enhance the cleaning/sanitization properties and should lengthen the time before the blended EA water neutralizes due to the increased activity in the water. Alternatively, for example, the liquid can be passed more quickly through the functional generator while retaining substantially the same cleaning/sanitizing power.

10. EXAMPLE HOUSING FOR COMBINED SPARGING DEVICE AND FUNCTIONAL GENERATOR, WHICH BLENDS THE OUTPUTS

Figure 8A:
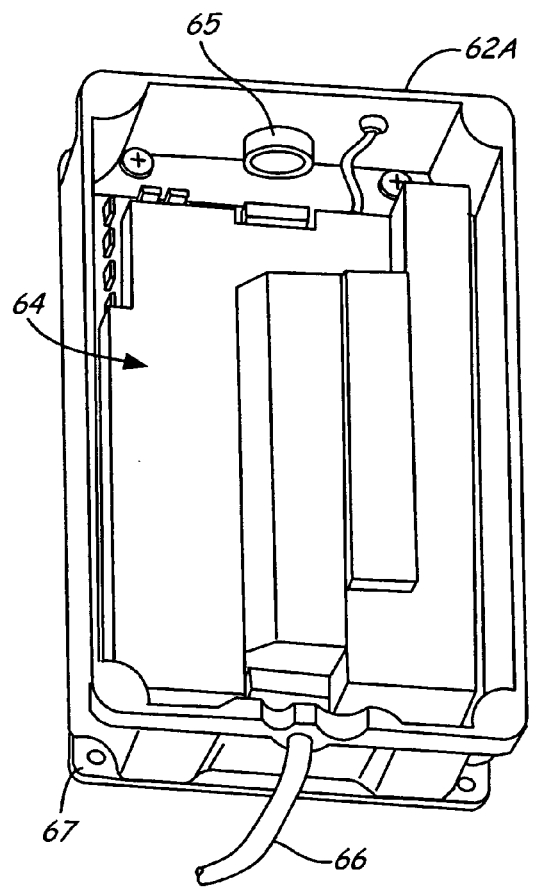
FIGS. 8A and 8B together illustrate a housing containing a sparging device and a functional generator according to an embodiment of the disclosure.
Figure 8B:
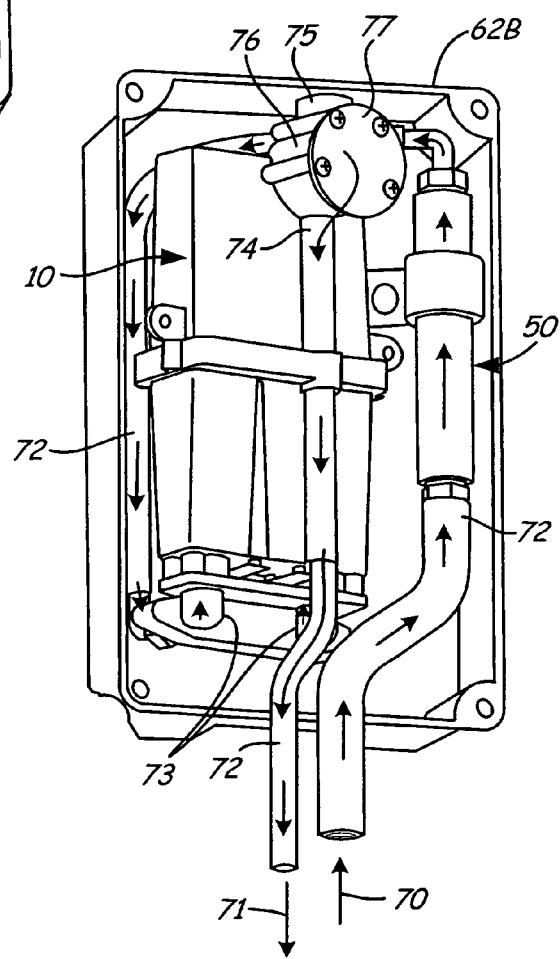

FIGS. 8A and 8B together illustrate a housing formed by clamshell halves 62A and 62B, which together form a generally water-tight housing containing control electronics 64, functional generator 10 and sparging device 50. Housing 62 provides a convenient, compact housing for both functional generator 10 and sparging device 50 and their related control electronics 64. However, these devices can be mounted separately in other embodiments.

Control electronics 64 includes a printed circuit board containing electronic devices for powering and controlling the operation of functional generator 10 and sparging device 50. Housing half 62A includes an access port 65, which provides access to one or more electrical test points, and a cable 66, which provides wire connections for powering control electronics 64 and devices 10 and 50 and for controlling further elements, such as one or more pumps or valves, outside of housing 62. Housing half 62A can further include a cover plate 67 for providing a heat sink for control electronics 64. Plate 67 can further include a plurality of fins for providing additional cooling, and can also be modified to support a cooling fan, if desired. In other embodiments, a cooling fan can be provided in, on or near any other location of housing 62.

In one example, control circuit 64 includes a power supply having an output that is coupled in parallel with functional generator 10 and sparging device 50 and which limits the power delivered to the two devices to 150 Watts, for example. Control circuit 64 also includes an H-bridge that is capable of selectively reversing the polarity of the voltage applied to functional generator 10 and sparging device 50 as a function of a control signal generated by the control circuit. For example, control circuit 64 can be configured to alternate polarity in a predetermined pattern, such as every 5 seconds. Frequent reversals of polarity can provide a self-cleaning function to the electrodes, which can reduce scaling or build-up of deposits on the electrode surfaces and can extend the life of the electrodes.

In the example shown in FIG. 8B and similar to the example shown in FIG. 4, sparging device 50 is coupled upstream of functional generator 10. The arrows in FIG. 8B illustrate the flow path of liquid from an inlet 70 to an outlet 71. Sparging device 50 and functional generator 10 are coupled together, between inlet 70 and outlet 71 by various sections of tubing 72.

FIG. 8B illustrates an example of functional generator 10, which is implemented by modifying a commercially available cell, namely a JP102 cell from Emco Tech Co., LTD. Functional generator cell 10 has a housing that contains the electrode plates (e.g., as shown in FIG. 2) and has two inlets 73 and two outlets 74 and 75. One or both inlets 73 can be coupled to the sparging device 50. If one inlet is not used, that inlet can be capped closed. The output liquid produced by the anode and cathode chambers within generator 10 are supplied through separate ports to a chamber 76. A valve mechanism that is supplied with the JP102 cell (and selectively routes the anolyte and catholyte to separate, respective outlets 74 and 75) is removed from chamber 76, and chamber 76 is sealed with a cover plate 77 such that chamber 76 forms a mixing chamber that receives an anolyte from the anode chamber and a catholyte from the cathode chamber. The anolyte and catholyte mix together in chamber 76 to form a blended anolyte and catholyte EA water, which is directed from chamber 76 through to outlet 74 to outlet 71. Outlet 75 is capped closed. In another embodiment, the catholyte and anolyte outputs can be blended downstream of functional generator cell 10 or left as separate streams through outlets 44 and 45, for example.

Figure 9A:
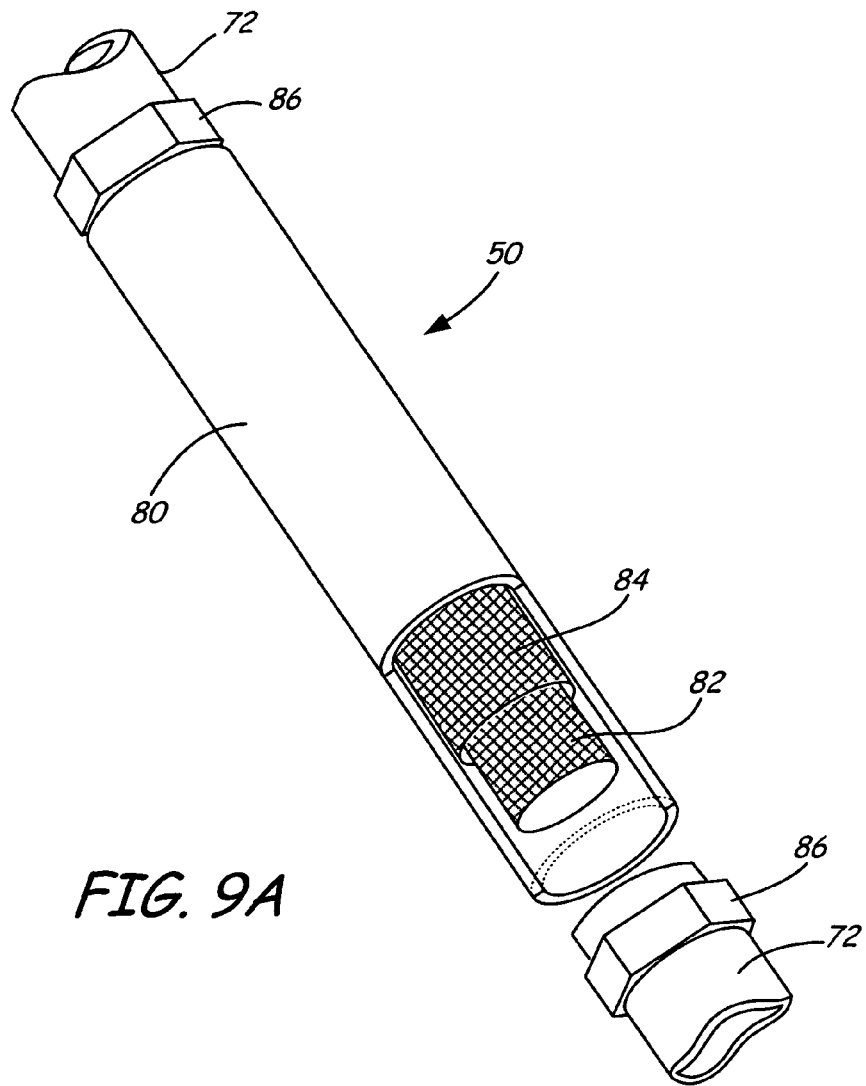
FIG. 9 is a perspective view of the sparging device shown in FIG. 8B.

In the example shown in FIG. 8B, sparging device 50 has a tubular shape. FIG. 9A illustrates sparging device 50 in greater detail according to one illustrative example, wherein portions of device 50 are cut away for illustration purposes. In this example, sparging device 50 is an electrolysis cell having a tubular outer electrode 80 and a tubular inner electrode 82, which are separated by a suitable gap, such as 0.020 inches. Other gap sizes can also be used. In one example, outer electrode 80 has a solid plate construction, inner electrode 82 has a wire mesh construction, and the two electrodes are separated by a tubular dielectric mesh 84. For example, outer electrode 80 can include a titanium plate spattered with platinum, and inner electrode 82 can include a mesh of #304 stainless steel having a 1/16-inch grid. Other materials, electrode shapes and dimensions. In this example, the mesh construction of elements 82 and 84 enhances liquid flow within the gap between the two electrodes. This liquid flow is conductive and completes an electrical circuit between the two electrodes. Electrolysis cell 50 can have any suitable dimensions. In one example, cell 50 can have a length of about 4 inches long and an outer diameter of about 3/4 inch. The length and diameter can be selected to control the treatment time and the quantity of nanobubbles or microbubbles generated per unit volume of the liquid. Alternatively, for example, both electrodes can be tubular meshes, if the cell is housed in an outer lumen that contains the liquid. In a further example, the inner electrode includes a bare wire that is coaxial with the outer electrode. Numerous variations can be utilized.

Cell 50 can be coupled at any suitable location along the liquid flow path, such as by splicing the cell between two pieces of conduit such that the liquid flows through the cell, in the direction of the arrows shown in FIG. 8B. Any method of attachment can be used, such as through plastic quick-connect fittings 86.

Figure 9B:
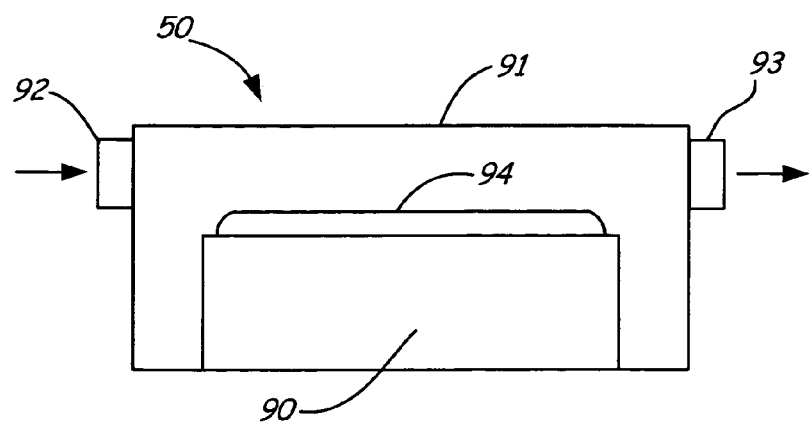

FIG. 9B illustrates sparging device 50 according to another embodiment of the disclosure. In one example shown in FIG. 9B, sparging device 50 includes a commercially available oxygenator 90, which is mounted within a container 91 having an inlet 92 and an outlet 93. For example, oxygenator 90 can include the OXYGENATOR Bait Keeper available from Aqua Innovation, Inc. of Bloomington, Minn., which is described in more detail in Senkiw U.S. Pat. No. 6,689,262. Oxygenator 90 has a pair of externally-exposed electrodes 94 formed by a planar, circular wire mesh and a planar, circular plate that are parallel to one another and separated by a small gap to form a reaction chamber. Container 91 can be positioned at any suitable location along the liquid flow path.

11. EXAMPLE OF A HARD AND/OR SOFT FLOOR CLEANING SYSTEM

The various functional generators and sparging devices discussed above can be implemented in a variety of different types of cleaning or sanitizing systems. For example, they can be implemented on an onboard (or off-board) mobile (or immobile) surface cleaner, such as a mobile hard floor surface cleaner, a mobile soft floor surface cleaner or a mobile surface cleaner that is adapted to clean both hard and soft floors or other surfaces, for example.

Figure 10A:
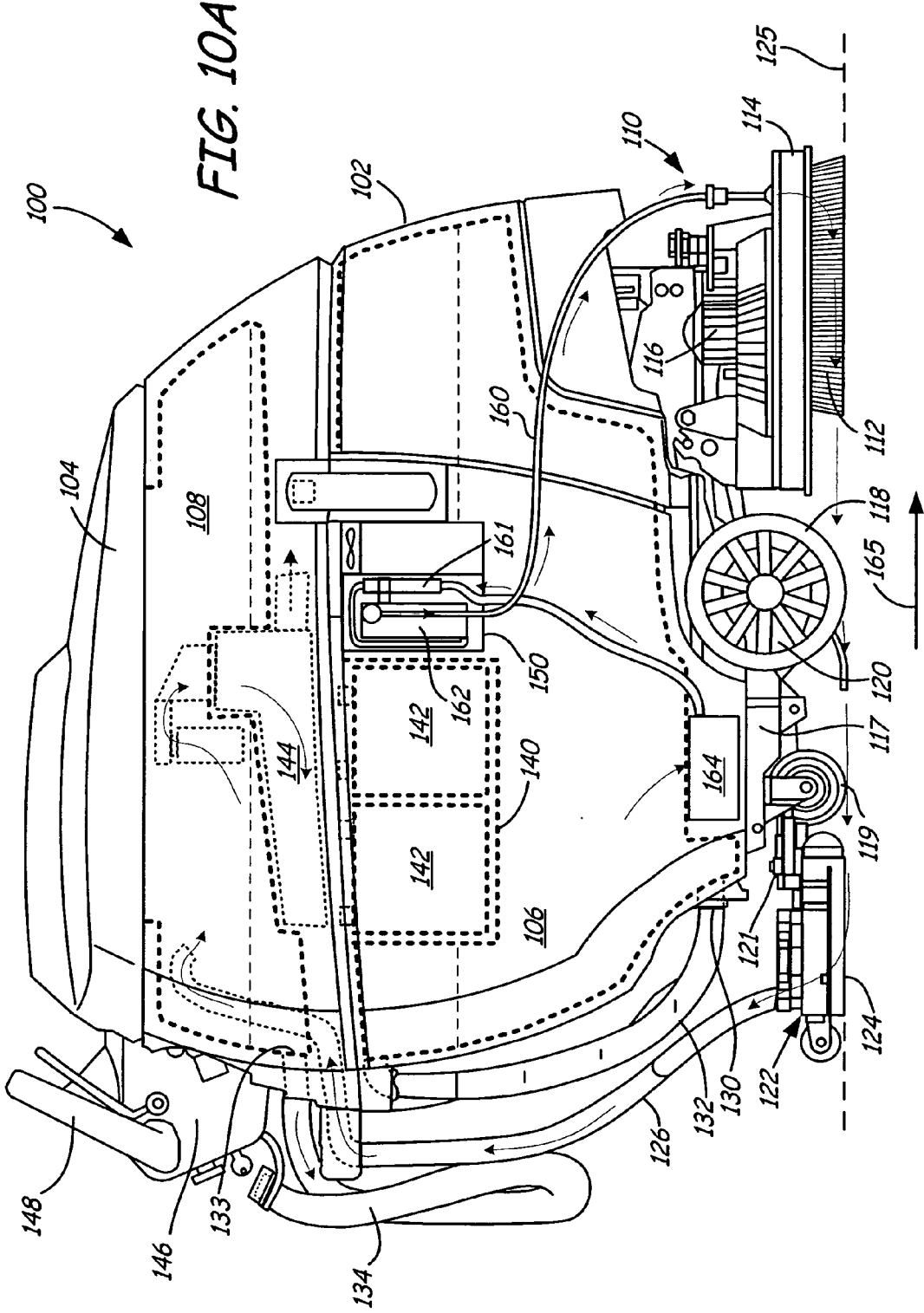
FIG. 10A is a side elevation view of a mobile hard floor surface cleaner in accordance with one or more exemplary embodiments of the disclosure.
Figure 10B:
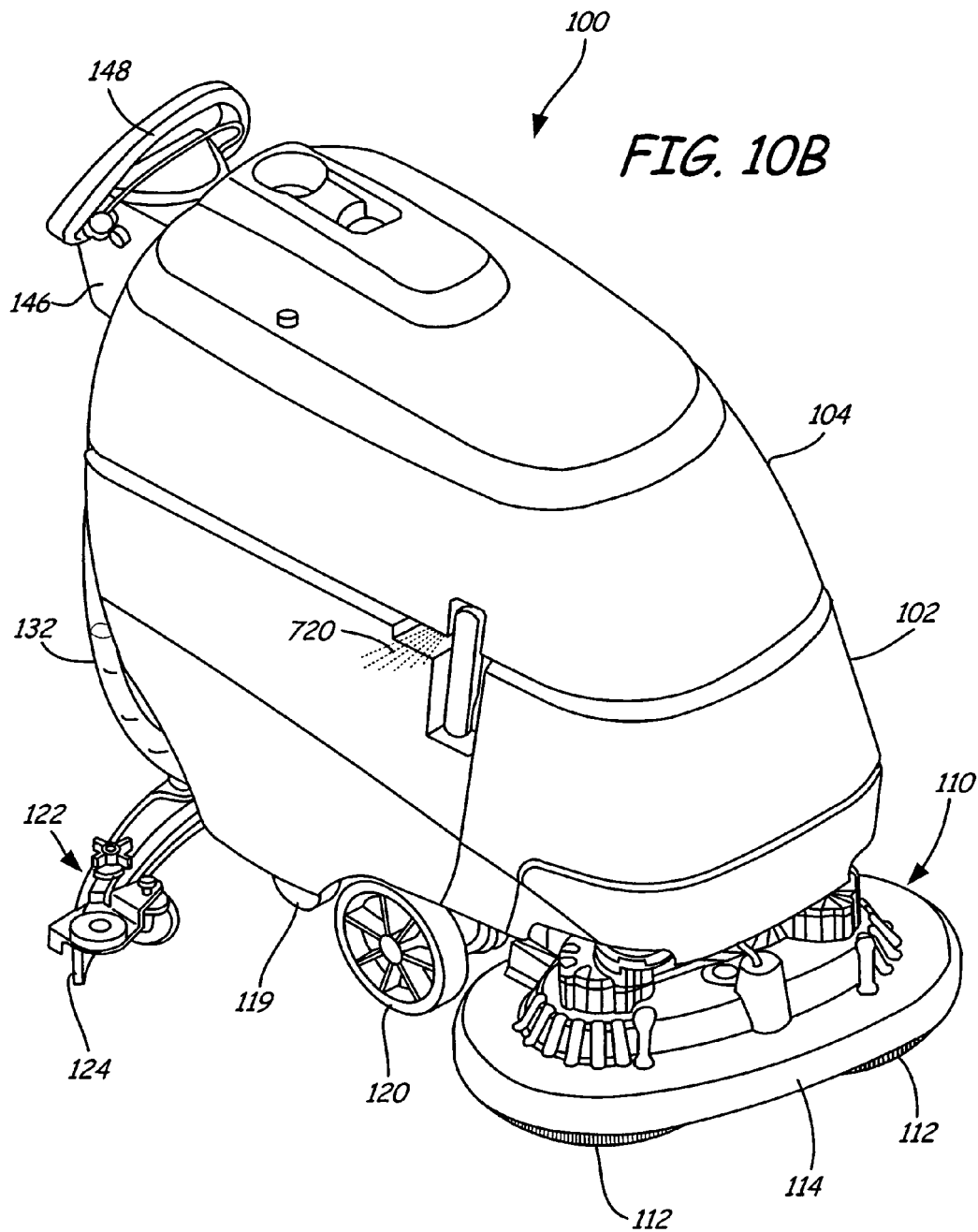
FIG. 10B is a perspective view of the mobile hard floor surface cleaner shown in FIG. 10A with its lid in a closed state.
Figure 10C:
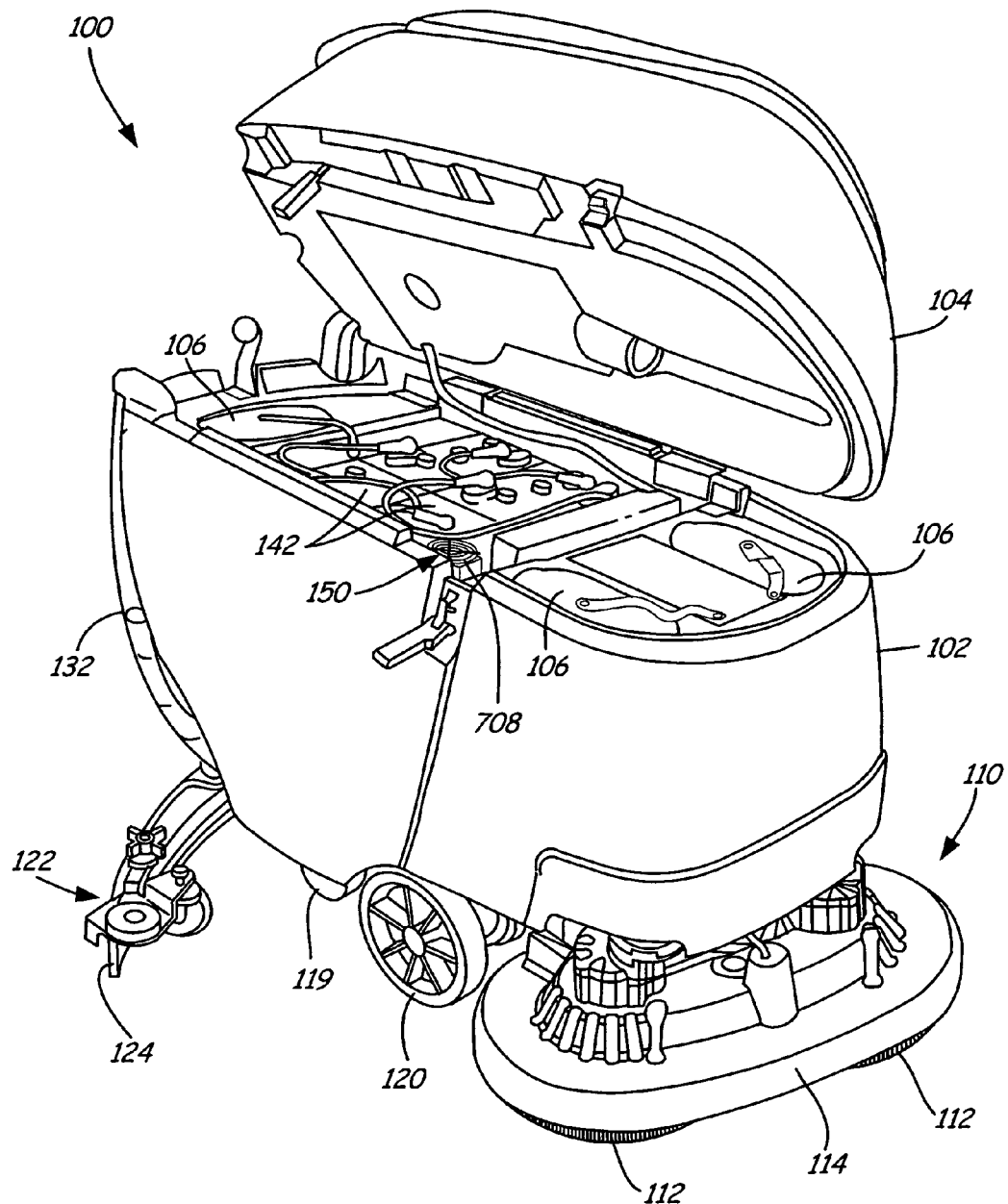
FIG. 10C is a perspective view of the mobile hard floor surface cleaner shown in FIG. 10A with its lid in an open state.

FIGS. 10A-10C illustrate a mobile hard floor surface cleaner 100 in accordance with one or more exemplary embodiments of the present disclosure. FIG. 10A is a side elevation view of cleaner 100. FIG. 10B is a perspective view of cleaner 100 having its lid in a closed position, and FIG. 10C is a perspective view of cleaner 100 having its lid in an open position.

In one example, cleaner 100 is substantially similar to the Tennant T5 Scrubber-Dryer as shown and described in the T5 Operator Manual Rev. 02, dated Sep. 9, 2006, and the T5 Parts Manual Rev. 02, dated Nov. 11, 2006, for example, which has been modified to include a sparging device and a functional generator, such as but not limited to those shown in FIGS. 8A and 8B or any of the other embodiments shown or described herein and/or combinations thereof.

In this example, cleaner 100 is a walk-behind cleaner used to clean hard floor surfaces, such as concrete, tile, vinyl, terrazzo, etc. Alternatively, for example, cleaner 100 can be configured as a ride-on, attachable, or towed-behind cleaner for performing a scrubbing operation as described herein. In a further example, cleaner 100 can be adapted to clean soft floors, such as carpet, or both hard and soft floors in further embodiments. Cleaner 100 may include electrical motors powered through an on-board power source, such as batteries, or through an electrical cord. Alternatively, for example, an internal combustion engine system could be used either alone, or in combination with, the electric motors.

Cleaner 100 generally includes a base 102 and a lid 104, which is attached along one side of the base 102 by hinges (not shown) so that lid 104 can be pivoted up to provide access to the interior of base 102. Base 102 includes a tank 106 for containing a liquid or a primary cleaning and/or sanitizing liquid component (such as regular tap water) to be treated and applied to the floor surface during cleaning/sanitizing operations. Alternatively, for example, the liquid can be treated onboard or offboard cleaner 100 prior to containment in tank 106. Tank 106 can have any suitable shape within base 102, and can have compartments that at least partially surround other components carried by base 102.

Base 102 carries a motorized scrub head 110, which includes one or more scrubbing members 112, shrouds 114, and a scrubbing member drive 116. Scrubbing member 112 may include one or more brushes, such as bristle brushes, pad scrubbers, microfibers, or other hard (or soft) floor surface scrubbing elements. Drive 116 includes one or more electric motors to rotate the scrubbing member 112. Scrubbing members 112 may include a disc-type scrub brush rotating about a generally vertical axis of rotation relative to the floor surface, as shown in FIGS. 10A-10C. Alternatively, for example, scrubbing members 112 may include one or more cylindrical-type scrub brushes rotating about a generally horizontal axis of rotation relative to the hard floor surface. Drive 116 may also oscillate scrubbing members 112. Scrub head 110 may be attached to cleaner 100 such that scrub head 110 can be moved between a lowered cleaning position and a raised traveling position. Alternatively, for example, cleaner 100 can include no scrub head 110 or scrub brushes.

Base 102 further includes a machine frame 117, which supports source tank 106 on wheels 118 and castors 119. Wheels 118 are driven by a motor and transaxle assembly, shown at 120. The rear of the frame carries a linkage 121 to which a fluid recovery device 122 is attached. In the embodiment of FIGS. 10A-10C, the fluid recovery device 122 includes a vacuum squeegee 124 that is in vacuum communication with an inlet chamber in recovery tank 108 through a hose 126. The bottom of source tank 106 includes a drain 130, which is coupled to a drain hose 132 for emptying source tank 106. Similarly, the bottom of recovery tank 108 includes a drain 133, which is coupled to a drain hose 134 for emptying recovery tank 108. Alternatively, for example, one or both of the source tank and recovery tank and related systems can be housed in or carried by a separate apparatus.

In a further exemplary embodiment, the fluid recovery device includes a non-vacuumized mechanical device for lifting the soiled solution away from the floor surface and conveying the soiled solution toward a collection tank or receptacle. The non-vacuumized mechanical device can include, for example, a plurality of wiping media such as pliable material elements, which are rotated into contact with the floor surface to engage and lift the soiled solution from the floor surface.

In a further embodiment, cleaner 100 is equipped without a scrub head, wherein the liquid is dispensed to floor 125 for cleaning or sanitizing without a scrubbing action. Subsequently, fluid recovery device 122 recovers at least part of the dispensed liquid from the floor.

In another embodiment, cleaner 100 includes a wand sprayer and extractor or other attachment (not shown) that can be used to clean off-floor surfaces.

Cleaner 100 can further include a battery compartment 140 in which batteries 142 reside. Batteries 142 provide power to drive motors 116, vacuum fan or pump 144, and other electrical components of cleaner 100. Vacuum fan 144 is mounted in the lid 104. A control unit 146 mounted on the rear of the body of cleaner 100 includes steering control handles 148 and operating controls and gages for cleaner 100.

Liquid tank 106 is filled with a liquid to be treated for cleaning and/or sanitizing use, such as regular tap water. In one embodiment, the liquid is free of any surfactant, detergent or other cleaning chemical. Cleaner 100 further includes an output fluid flow path 160, which includes a pump 164, a sparging device 161 and a functional generator 162. Tank 106, sparging device 161, functional generator 162 and pump 164 can be positioned anywhere on cleaner 100. In one embodiment, sparging device 161 and functional generator 162 are similar to those shown in FIGS. 8A and 8B and are mounted within a housing 150 that is carried within base 102. Pump 164 is mounted beneath source tank 106 and pumps water from tank 106 along flow path 160, through sparging device 161 and functional generator 162 to the vicinity of scrub head 110 an ultimately to floor 125, wherein recovery device 122 recovers the soiled liquid and returns it to recovery tank 108. The arrows in FIG. 10A illustrate the direction of liquid flow from tank 106, through flow path 160, to floor 125 and then from recovery device 122 to recovery tank 128. Alternatively, for example, a second sparging device 163 (shown in FIG. 11) can be positioned downstream of functional generator 162. Similarly, pump 164 can be positioned downstream or upstream of any of the components along flow path 160. Alternatively, for example, pump 164 can be removed and the flow path 160 configured such that water passes along flow path 160 by the operation of gravity. Any suitable type or model of pump can be used. For example, pump 164 can include a SHURflo SLV10-AB41 diaphragm pump (available from SHURflo, LLC of Cypress Calif.) having an open flow capacity of 1.0 gallons/minute (gpm). In this example, a pump having a small open flow capacity can be used since the flow path 160 in this example has little or no back pressure. When enabled, pump 164 can be controlled to pump at any suitable rate, such as at any rate greater than zero gpm and up to 1.0 gpm. For example the rate can be set to a predetermined rate or an adjustable rate within the range of 0.1 gpm to 1.0 gpm, or within the range of 0.15 gpm to 0.75 gpm. Larger rates can be achieved with larger pumps, if desired.

In one embodiment of the disclosure, the control unit 146 is configured to operate pump 164, sparging device 161 and functional generator 162 in an "on demand" fashion. Pump 164 is in an "off" state and sparging device 161 and functional generator 162 are de-energized when cleaner 100 is at rest and not moving relative to the floor being cleaned. Control unit 146 switches pump 164 to an "on" state and energizes sparging device 161 and functional generator 162 when cleaner 100 travels in a forward direction relative to the floor, as indicated by arrow 165. In the "on" state, pump 164 pumps water from tank 106 through flow path 160 to the vicinity of scrub head 110. Thus, sparging device 161 and functional generator 162 generate and deliver EA water "on demand".

As the water passes along flow path 160, sparging device 161 and functional generator 162 temporarily restructure the water by injecting nanobubbles into the water so that it becomes highly oxygenated and by electrochemically activating the water and separating the activated water into a catholyte output stream and an anolyte output stream. The functional generator changes the oxidation reduction potential (ORP) of the catholyte and anolyte output streams. As discussed above, normal tap water is made of large conglomerates of unstructured water molecules, which are too large to move efficiently without a surfactant to break the water's surface tension. The catholyte output stream becomes highly alkaline with a pH of about 11, for example, and is structured with smaller clusters of water molecules, which penetrate at a much faster rate when used for cleaning purposes. The alkaline water is abundant with electrons and is called reducing water. It has the capacity to penetrate dirt molecules and clean surfaces, mimicking a surfactant-based cleaning solution. The anolyte output stream becomes highly acidic, with a pH of about 3, for example. The resulting acidic water lacks electrons and is called oxidizing water. As such, the acidic water has the capacity to reduce bacteria and other harmful organisms by depriving them of electrons.

In one embodiment, the catholyte and anolyte output streams are recombined at the output of functional generator 162, is discussed with respect to FIGS. 8A and 8B, and flow path 160 then dispenses the resulting blended catholyte and anolyte EA water to scrub head 110 or directly to the floor being cleaned.

Alternatively, for example, one or more tanks 106 can be filled with sparged water, non-sparged EA water (catholyte and/or anolyte), or sparged EA water, which is then dispensed by cleaner 100. For example, tank 106 can be filled from a previously-sealed container of EA water or can be filled from a nearby stationary or mobile "filling station", which carries a functional generator for electrochemically activating water and then loading the tank 106 through a hose or other temporary attachment to cleaner 100. An additive, if needed, can be added to the pre-electrochemically activated water to maintain the electrochemically activated state. In the case in which tank 106 is filled with sparged non-EA water, cleaner 100 can include a functional generator to electrochemically activate the water prior to dispensing the water. In the case in which tank 106 is filled with non-sparged EA water, cleaner 100 can dispense the non-sparged EA water without further treatment or can include a sparging device to sparge the water prior to dispensing the water. If tank 106 is filled with sparged EA water, cleaner 100 can dispense the liquid with or without further treatment by an onboard functional generator and/or an onboard sparging device. Alternatively, for example, an additional sparging device can be implemented onboard the cleaner to sparge the EA water prior to distribution.

As described in more detail below, flow path 160 can include a single, combined output flow path for the blended catholyte and anolyte EA water produced at the output of functional generator 162 or can include separate paths that can combine somewhere along flow path 160 or at the dispenser or remain separate along the entire length of flow path 160. The separate flow streams can have a common fluid dispenser near scrub head 110 or can be routed to separate liquid dispensers. Pump 164 can represent a single pump or multiple pumps for multiple flow paths.

In an embodiment in which cleaner 100 is configured to selectively dispense one or both the anolyte or catholyte EA water outputs, cleaner 100 can also include one or more waste water flow paths from functional generator 162 for routing unused catholyte or anolyte EA water from housing 150 to recovery tank 108 or a separate waste water tank. A flow path can also be provided for routing unused catholyte or anolyte to a buffer or reservoir (not shown in FIGS. 10A-10C) for later use by cleaner 100. For example if cleaner 100 is operated in a cleaning only mode, the anolyte EA water produced by functional generator 162 is not needed and can be routed to recovery tank 108 or to a buffer or separate storage tank for later use, such as in a disinfecting operating mode.

If cleaner 100 is operated in a disinfecting only mode, the catholyte EA water produced by functional generator is not needed and can be routed to recovery tank 108 or to a buffer or separate storage tank for later use, such as in a cleaning operating mode. In a cleaning and disinfecting operating mode, both the catholyte EA water and the anolyte EA water are routed along flow path 160 to be applied to the floor either simultaneously or sequentially. The catholyte EA water can be applied to the floor surface to clean the floor surface and then removed prior to application of the anolyte EA water to the same floor surface for disinfecting purposes. The catholyte and anolyte EA water can also be applied in a reverse order. Alternatively, for example, cleaner 100 can be configured to apply intermittently catholyte EA water for a short period of time followed by application of anolyte EA water, or vice versa. The various operating modes that control whether catholyte and/or anolyte EA water are applied and at what times, concentrations, flow rates and proportions (such as those described with reference to FIG. 2) can be controlled by the operator through control unit 146.

In a further embodiment, cleaner 100 can be modified to include two separate cleaning heads, one for dispensing and recovering anolyte EA water and one for dispensing and recovering catholyte EA water. For example, each head would include its own liquid dispenser, scrub head and squeegee. One can follow the other along the travel path of the cleaner. For example, the leading head can be used for cleaning, while the trailing head can be used for sanitizing.

However in the example shown in FIG. 8, the two output streams are combined at the output of functional generator 162 with no separate control of each output stream.

It has been found that when the two liquids streams containing the anolyte EA water and the catholyte EA water are applied to the surface being cleaned at the same time, either through a combined output stream or separate output streams, the two liquids, although blended or combined on the surface, retain their individual enhanced cleaning and sanitizing properties during a typical resident time on the surface. For example, as cleaner 100 advances at a typical rate across the surface being cleaned, the residence time on the surface between distribution to the surface and then recovery by vacuum squeegee 124 is relatively short, such as about three seconds. In one example, the catholyte EA water and the anolyte EA water maintain their distinct electrochemically activated properties for at least 30 seconds, for example, even though the two liquids are blended together. During this time, the distinct electrochemically activated properties of the two types of liquids do not neutralize until after the liquid has been recovered from the surface. This allows the advantageous properties of each liquid to be utilized during a common cleaning operation.

After recovery, the nanobubbles begin to diminish and the alkaline and acidic liquids begin to neutralize. Once neutralized, the electrochemical properties, including the pH, of the recovered, blended liquid reverts to those of regular tap water.

Sparging device 161 and functional generator 162 can be powered by batteries 142 or by one or more separate power supplies that are powered by or independent of batteries 142 and adapted to provide the electrodes with the desired voltage and current levels in a desired waveform. In one example, sparging device 161 and functional generator 162 are electrically coupled in parallel with one another and powered by batteries 142 through a control circuit such as that shown in FIG. 8A, which intermittently reverses the polarity applied to the devices.

The liquid distribution path of cleaner 100 can also include, if desired, one or more filters for removing selected components or chemicals from the feed water or the produced EA water to reduce residue left on the surface being cleaned. The path can also include an ultraviolet (UV) radiation generator for UV-treating the liquid to reduce viruses and bacteria in the liquid.

Figure 11:
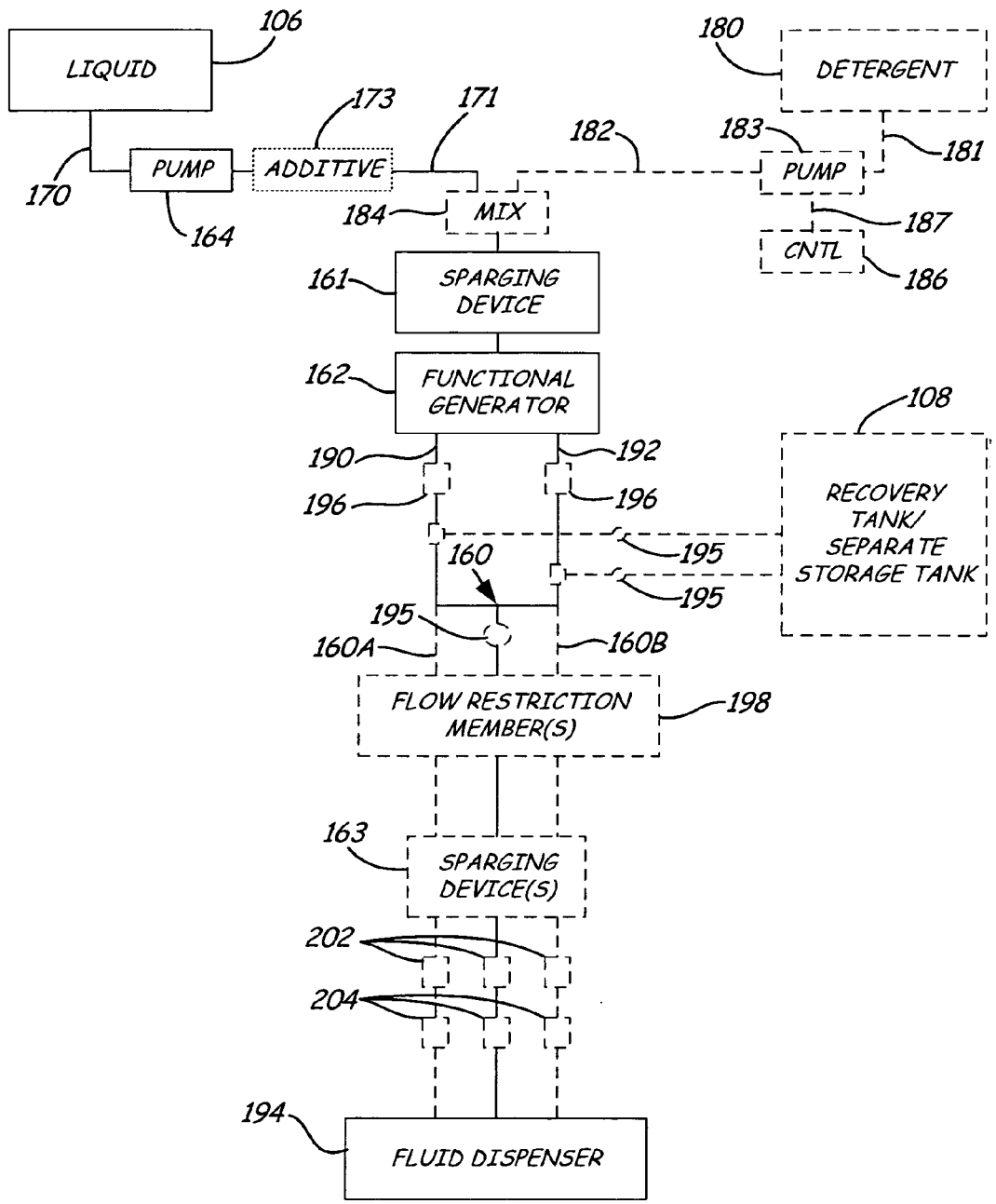
FIG. 11 is a block diagram illustrating a liquid distribution flow path of the cleaner shown in FIGS. 10A-10C in greater detail according to an embodiment of the disclosure.

FIG. 11 is a block diagram illustrating the liquid distribution flow path 160 of cleaner 100 in greater detail according to an embodiment of the disclosure. For simplicity, the wastewater flow path to recovery tank 108 and other components of cleaner 100 are not illustrated in FIG. 11. The elements in flow path 160 can be rearranged upstream or downstream relative to one another in other embodiments. Also, the particular elements along flow path 160 may vary greatly from one embodiment to the next, depending upon the particular application and platform being implemented. Some elements may be removed, while others can be added. For example, in one embodiment, sparging device 161 may be eliminated, while in another embodiment, functional generator 162 may be eliminated. The elements shown in dashed lines are not present in the example shown in FIGS. 10A-10C, but may be included in other embodiments. The embodiment shown in FIG. 11 is merely exemplary.

The liquid or feed water in tank 106 is coupled to the input of functional generator 162 through conduit sections 170, 171, pump 164 and sparging device 161. Pump 164 can include any suitable type of pump, such as a diaphragm pump. Other types of pumps can also be used.

As discussed above, an additive or boosting compound, such as an electrolyte (e.g., sodium chloride) or other compound, can be added to the feed water at any desired concentration and at any desired location along the flow path upstream of functional generator 162. For example, the additive can be added to the water within tank 106. in a further example, an additive flow-through device 173 can be coupled in-line with the flow path, such as downstream (or upstream) of pump 164 for inserting the additive into the feed water. However, such an additive is not required for many cleaning applications and types of liquid, such as regular tap water. In some applications an additive can be used to further boost the respective pH values of the anolyte and catholyte outputs of the functional generator even further away from a neutral pH, if desired.

Sparging device 161 can be located anywhere along the flow path between liquid source 106 and functional generator 162, or anywhere downstream of functional generator 162. In one embodiment, sparging device includes an electrolysis cell, such as that shown in FIG. 9A or 9B for sparging the liquid by electrolysis. However, other types of sparging devices can also be used, such as those discussed above.

In applications in which an additional detergent is desired, cleaner 100 can be modified to further include a source 180 of a cleaning agent, which is supplied to the input of functional generator through conduit sections 181, 182 and pump 183

(all shown in dashed lines). Alternatively, for example, pump 183 can supply the cleaning agent to one or more of the flow paths 160 downstream of functional generator 162 or to the flow path upstream of pump 164, for example. Mixing member 184 mixes the supplied cleaning agent with the feed water from liquid source 106.

The flow of cleaning agent is generated substantially independently of the volume of cleaning agent in supply 180. A check valve (not shown) can be installed in line with conduit section 170 to prevent the back flow of cleaning agent and primary cleaning liquid component to tank 106 when fluid mixing member 184 is upstream of pump 164. Pump 183 can include any suitable pump, such as a solenoid pump. An example of a suitable solenoid pump is pump number ET200BRHP sold through Farmington Engineering of Madison, Conn. and manufactured by CEME. Another suitable pump is the SV 653 metering pump manufactured by Valcor Scientific. Other types of pumps can also be used for pump.

A controller 186 (shown in dashed lines) controls the operations of pump 183 through a control signal 187. One suitable controller is part number QRS2211C (either 24V of 36V) sold by Infitec Inc. or Syracuse, N.Y. In accordance with one embodiment, signal 187 is a pulsed signal that provides power relative to ground (not shown) and controls the duration over which the pump drives the cleaning agent through conduit 182. For example, control signal 187 can turn pump 183 on for 0.1 seconds and off for 2.75 seconds to produce a low volume output flow of concentrated cleaning agent. Other on/off times can also be used. In addition, pumps 164 and 183 can be eliminated and the liquid and cleaning agent can be fed by another mechanism, such as gravity. In the example shown in FIGS. 100A-10C, cleaner 100 does not include elements 180, 183, 184 and 186 since no additional cleaning agent is used.

Functional generator 162 has a catholyte EA water output 190 and an anolyte EA water output 192, which are combined into a common flow path 160 (shown in solid lines) and fed to a fluid dispenser 194. In another embodiment of the disclosure, flow path 160 includes a separate flow path 160A and 160B (shown in dashed lines) for each output 190 and 192. The relative flows through the individual or combined flow paths can be controlled through one or more valves or other flow control devices 195 placed along the paths.

Buffers or reservoirs 196 can be placed along paths 160, 160A and/or 160B to collect any catholyte or anolyte produced by functional generator 162 but not immediately delivered to fluid dispenser 194. For example, reservoirs 196 can include a burp valve, which allows the reservoir to fill, then once filled, empty into the respective flow path for use. Other types of reservoirs and valve or baffle systems can also be used. The two reservoirs 196 can be controlled to open or empty alternately, simultaneously, or on any other interval or control signal. If one of the catholyte or anolyte is not being used for a particular cleaning or sanitizing operation, the excess unused liquid can be supplied to recovery tank 108, through valves 195. Alternatively, for example, the liquid can be supplied to a separate storage tank for later use. A separate storage tank can also be used, for example, in embodiments in which the output flow rate of the dispenser exceeds the rate at which one or more of the elements in the flow path can treat the liquid to be dispensed effectively.

In accordance with another embodiment of the disclosure, one or more flow restriction members 198 can be placed in line with flow paths 160, 160A and/or 160B to regulate the flow of liquid if desired or needed for a particular configuration. For example, a pressure drop across flow restriction members 198 can restrict the flow of fluid to provide the desired volume flow rate. For example, a flow restriction member 198 can include a metering orifice or orifice plate that provides a desired output flow, such as of 0.2 GPM, for example, when the pressure of outlet of pump 164 is at approx. 40 psi. Other flow rates greater than or less than 0.2 GPM can also be used.

If a supply of cleaning agent is used, the volume flow rate of cleaning agent can be limited by pump 183 to approximately 10 cubic centimeters or less per minute, for example. Examples of elements and methods for controlling the volume flow rates of the liquid and the cleaning agent are described in more detail in U.S. Pat. No. 7,051,399. However, these elements and methods are not required in one or more embodiments of the present disclosure.

In addition to or in replace of sparging device 161, cleaner 100 can further include one or more sparging devices 163 along combined flow path 160 or along one or both the separate flow paths 160A and 160B, downstream of functional generator 162. Sparging devices 163 can be located anywhere along flow paths 160, 160A and 160B between functional generator 162 and fluid dispenser 194. In one embodiment, sparging devices 163 include an electrolysis cell, such as that shown in FIG. 9A or 9B for sparging the liquid by electrolysis. However, other types of sparging devices can also be used.

Flow paths 160, 160A and/or 160B can further include pressure relief valves 202 and check valves 204, which can be located at any suitable position along any flow path in cleaner 100. Check valves 204 can help to limit leakage of liquid when cleaner 100 is not in use.

Fluid dispenser 194 can include any suitable distribution elements for the particular application in which cleaner 100 is used. For example in one embodiment, fluid dispenser 194 directs the liquid to the hard floor surface or to another component of cleaner 100, such as a scrub head. In the case in which the scrub head has multiple brushes, fluid dispenser 194 can include a T-coupling, for example, can be used to route separate output streams to each brush, if desired. The liquid can be dispensed in any suitable manner, such as by spraying or dripping.

In embodiments in which the anolyte and catholyte are applied separately from one another, fluid dispenser 194 can have separate outputs, one for each type of liquid. Alternatively, for example, fluid dispenser can have a single output, where the flow from each flow path is controlled by a valve, switch or baffle, for example. In a further embodiment, fluid dispenser 194 includes a flow control device that selectively passes the anolyte only, the catholyte only or a mixture of the anolyte and catholyte. The terms fluid dispenser and liquid dispenser can include, for example, a single dispensing element or multiple dispensing elements whether or not those elements are connected together.

It has also been found that the fine gas bubbles, such as nanobubbles, produced by any one of the sparging devices 161 and 163 can further delay neutralization of the anolyte EA water and the catholyte EA water when the two liquids are applied to the surface being cleaned at the same time and blended together. This benefit can exist whether the liquid is distributed in separate flow paths or a combined flow path and whether the sparging device is upstream of functional generator 162, downstream of functional generator 162, in one or both of the downstream flow paths 160A and 160B, a combined flow path 160, or any combination of these locations.

It has been found that when the two liquids streams containing the anolyte EA water and the catholyte EA water are applied to the surface being cleaned at the same time, either through a combined output stream or separate output streams, the two liquids, although blended on the surface, retain their individual enhanced cleaning and sanitizing properties during a typical resident time on the surface. For example, when cleaner 100 advances at a typical rate across the surface being cleaned, the residence time on the surface between distribution to the surface and then recovery by vacuum squeegee 124 (shown in FIG. 10A) is relatively short, such as about 2-3 seconds. During this time, the distinct electrochemical activation properties of the two types of liquid do not neutralize until after the liquid has been recovered from the surface. This allows the advantageous properties of each liquid to be utilized during a common cleaning operation.

After recovery, the nanobubbles begin to diminish and the alkaline and acidic liquids begin to neutralize. Once neutralized, the electrochemical properties, including the pH, of the recovered, blended liquid reverts to those of regular tap water. This allows the oxidation-reduction potential and other beneficial cleaning/sanitizing properties of a blended EA water to be substantially retained during the residence time before these properties substantially neutralize in the recovery tank of the cleaner or following disposal.

Also, it has been found that the oxidation-reduction potential and other electrochemically activated properties of the blended EA water (or other EA liquid) neutralize relatively quickly in the recovery tank after recovery. This allows the recovered liquid to be disposed of almost immediately after a cleaning operation has been completed without having to wait or store the recovered liquid in a temporary disposal tank until the liquid neutralizes.

Cleaner 100 is simply one example of a surface cleaner with which one or more embodiments can be used. Other types of cleaners having a variety of other configurations and elements can be used in alternative embodiments of the present disclosure, such as those discussed below.

In a further embodiment, the liquid can be converted into an anolyte EA liquid and a catholyte EA liquid off-board cleaner 100. In this embodiment, cleaner 100 can be modified to include an anolyte source tank and a catholyte source tank for receiving the anolyte EA liquid and catholyte EA liquid generated by an off-board functional generator. Functional generator 162 can therefore be eliminated on cleaner 100. The outputs from the anolyte liquid tank and the catholyte liquid tank can be combined or maintained as separate output flows as described above. Cleaner 100 can include one or more sparging devices such as those shown in FIG. 11, if desired, to sparge the combined or separate output flows.

12. QUICK NEUTRALIZATION OF ANOLYTE AND CATHOLYTE OUTPUTS

A further aspect of the present disclosure is directed to a method in which a liquid, such as water, having a relatively neutral pH between pH6 and pH8, such as pH7, and a relatively neutral ORP between ±50 mV, such as 0 mV, is passed through a functional generator to produce an anolyte EA output and a catholyte EA output. The anolyte and catholyte EA outputs have pHs outside of the range between pH6 and pH8 and have ORPs outside the range of ±50 mV. For example, the anolyte EA output has a pH of about 2.5 to 6 and an ORP in a range of +100 mV to +1200 mV, +400 mV to +900 mV, or +400 mV to +700 mV. The catholyte EA output has a pH of about 8-12 and an ORP in a range of about −150 mV to −1000 mV, −150 mV to −700 mV, or −300 mV to −700 mV, for example.

The anolyte and catholyte EA outputs are applied to a surface for a residence time and then recovered from the surface and placed in a recovery tank. In one embodiment, the anolyte and catholyte EA outputs are applied to the surface within 5 seconds of the time at which the liquids are produced by the functional generator, and can be applied to the surface in a smaller time range, such as within 3 seconds of production. In one embodiment, the residence time on the surface is greater than zero seconds and less than 5 seconds, such as between 1-5 seconds, or between 2-3 seconds.

The anolyte and catholyte EA outputs can be blended prior to application to the surface, blended on the surface or blended in the recovery tank. For example, the anolyte and catholyte EA outputs can be applied to the surface simultaneously as a single, blended liquid or as separate liquids or can be applied and recovered sequentially, either overlapping or non-overlapping on the surface.

Once recovered, the blended anolyte and catholyte EA outputs within the recovery tank quickly neutralize substantially to the original pH and ORP of the source liquid (e.g., those of normal tap water). In one example, the blended anolyte and catholyte EA outputs within the recovery tank quickly neutralize substantially to a pH between pH6 and pH8 and an ORP between ±50 mV within a time window of less than 1 minute (such as within 30 seconds) from the time the anolyte and catholyte EA outputs are produced by the functional generator.

Thereafter, the recovered liquid can be disposed in any suitable manner. Similarly, in embodiments in which the liquid is not recovered from the surface being cleaned, the blended anolyte and catholyte EA outputs quickly neutralize on the surface substantially to the original pH and ORP of the source liquid. This method can be performed with cleaner 100 or any other apparatus, such as but not limited to those disclosed herein.

13. EXAMPLE OF A COMBINED HARD AND SOFT FLOOR CLEANER

Figure 12:
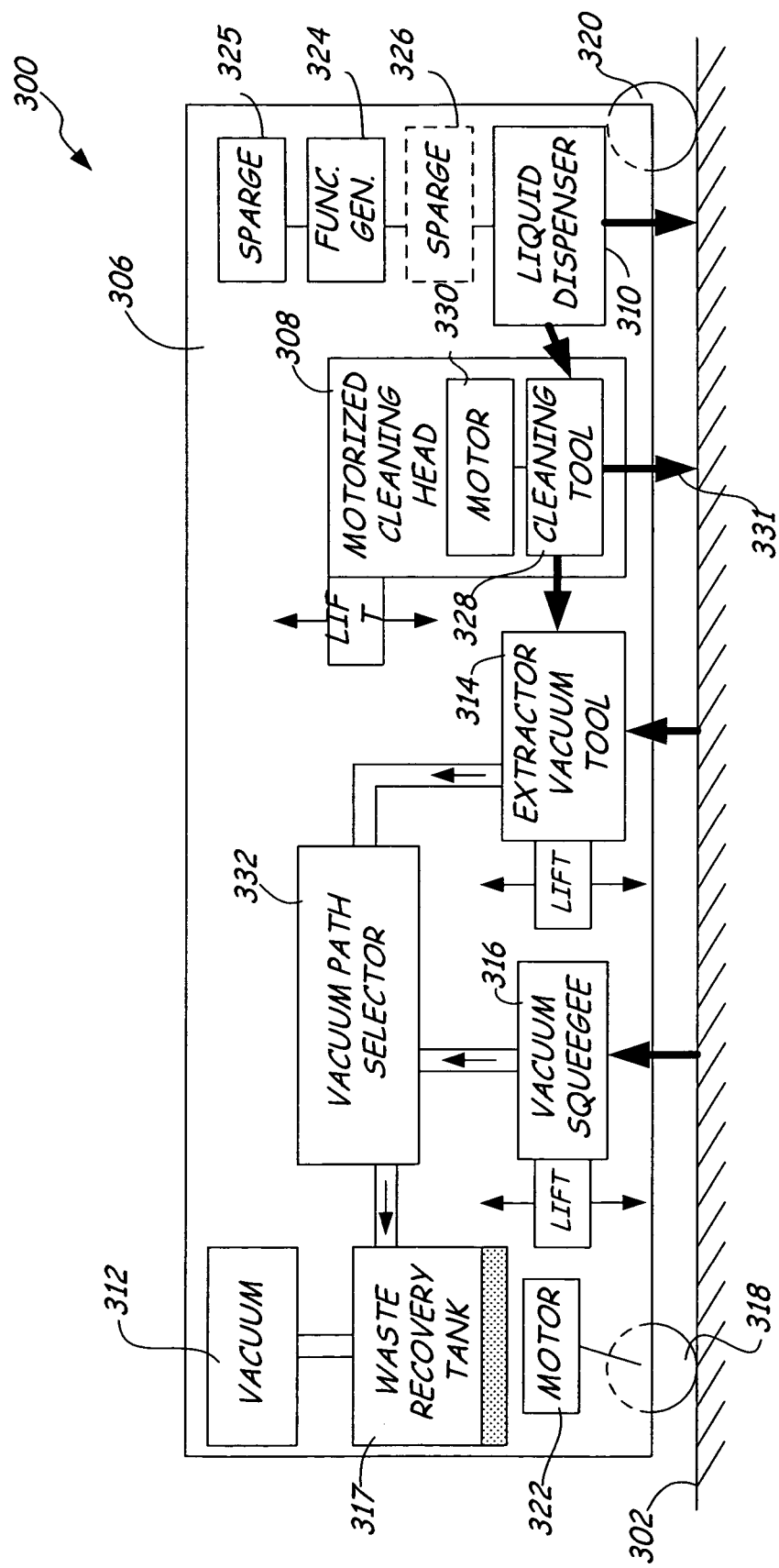
FIG. 12 is a block diagram of a floor cleaner that is configurable with multiple types of cleaning tools and extractors to accommodate different cleaning operations while using the same overall cleaner.

FIG. 12 is a block diagram of a floor cleaner 300 that is configurable with multiple types of cleaning tools and extractors to accommodate different cleaning operations while using the same overall cleaner.

Cleaner 300 can be configured in a soil transfer cleaning mode for performing a soil transfer cleaning operation on a soft floor surface, a deep extraction mode for performing a deep extraction cleaning operation, and a hard floor scrubbing mode for scrubbing a hard floor surface. In each of these modes, cleaner 300 removes liquid waste and debris with a fluid recovery system. However, all such components are not required in all embodiments of FIG. 12. The particular selection of components is provided as an example only.

Cleaner 300 can be configured for use by an operator that walks behind or rides on cleaner 300 or can be configured as a tow-behind cleaner, attached on to another device, be held by hand, or carried on a person, etc. Cleaner 300 may be powered through an on-board power source, such as batteries or an internal combustion engine, or powered though an electrical cord.

Floor cleaner 300 generally includes a mobile body 306, a motorized cleaning head 308, a liquid dispenser 310, one or more vacuums 312, at least one vacuum extractor tool 314, a vacuum squeegee 316 and a waste recovery tank 317.

The mobile body 306 is supported on drive wheels 318 and castor wheels 320 for travel over surface 302. In one embodiment, the drive wheels are driven by a motor 322.

Cleaner 300 has a liquid distribution path similar to one or more of the embodiments discussed with respect to FIGS. 8 and 9. Liquid dispenser 310 receives liquid, such as anolyte EA water, catholyte EA water, anolyte and catholyte EA water or blended anolyte and catholyte EA water, depending on the configuration, from a functional generator 324 and one or more sparging devices 325 and 326, as described above with respect to FIG. 9, for example. Alternatively, for example, cleaner 300 can include functional generator 324 without a sparging device or can include a sparging device without a functional generator. Dispenser 310 dispenses the liquid directly to floor 302 or to a component of cleaning head 308 through one or more nozzles or openings.

Cleaning head 308 includes a cleaning tool 328 and one or more motors 330 for driving rotation of the cleaning tool 328 about an axis that is either parallel or perpendicular to the surface 302, for example. The rotating cleaning tool 328 engages the surface 302 to perform a hard or soft floor cleaning operation, as indicated by arrow 331. Cleaning tool 328 may include one or more brushes, such as bristle brushes, pad scrubbers, microfibers, or other hard or soft floor surface scrubbing elements.

In accordance with one example, cleaner 300 includes a cleaning head lift, which lowers the cleaning head 308 for floor cleaning operations and raises the cleaning head 308 when not in use, such as during transport of the cleaner 300.

One embodiment of the cleaning head 308 is configured for use with multiple types of cleaning tools 328 in order to accommodate different cleaning operations while using the same motors 330, for example. Thus, the cleaning head 308 can be equipped with a soft floor cleaning tool 328 or a hard floor cleaning tool 328. Alternatively, for example, the cleaner 300 is configurable with separate soft and hard floor cleaning heads 308.

In a further embodiment, cleaner 300 can include a cleaning wand (not shown) in addition to or in place of cleaning head 308. The cleaning wand can include a first hose coupled to dispenser 310 for dispensing the EA water and a second hose coupled to the vacuum 312 for extracting soiled EA water from surface 302.

In the embodiment shown in FIG. 12, one or more vacuums 312 are used in combination with at least one vacuum extractor tool 314 to remove liquid and solid waste (i.e., soiled cleaning liquid) from cleaning tool 328 and/or surface 302. One vacuum 312 also operates with squeegee 316 to remove waste from surface 102. The waste is then deposited in one or more waste recovery tanks 317 or another location. In one embodiment, a single vacuum 312 is selectively coupled to squeegee 316 and extractor tool 314 using a vacuum path selector 332. In another embodiment, cleaner 300 includes separate vacuums 312 for vacuum squeegee 316 and extractor tool 314. One or more lifts may be provided to lift and lower each tool 314 and 316 out of and into operation.

In one embodiment, extractor tool 314 is used for removing liquid and solid debris from soft surfaces, whereas squeegee 316 is used for removing liquid and solid debris from hard surfaces. Other types of liquid and debris recovery tools and methods can also be used for use on hard surfaces, soft floor surfaces or both.

Figure 13:
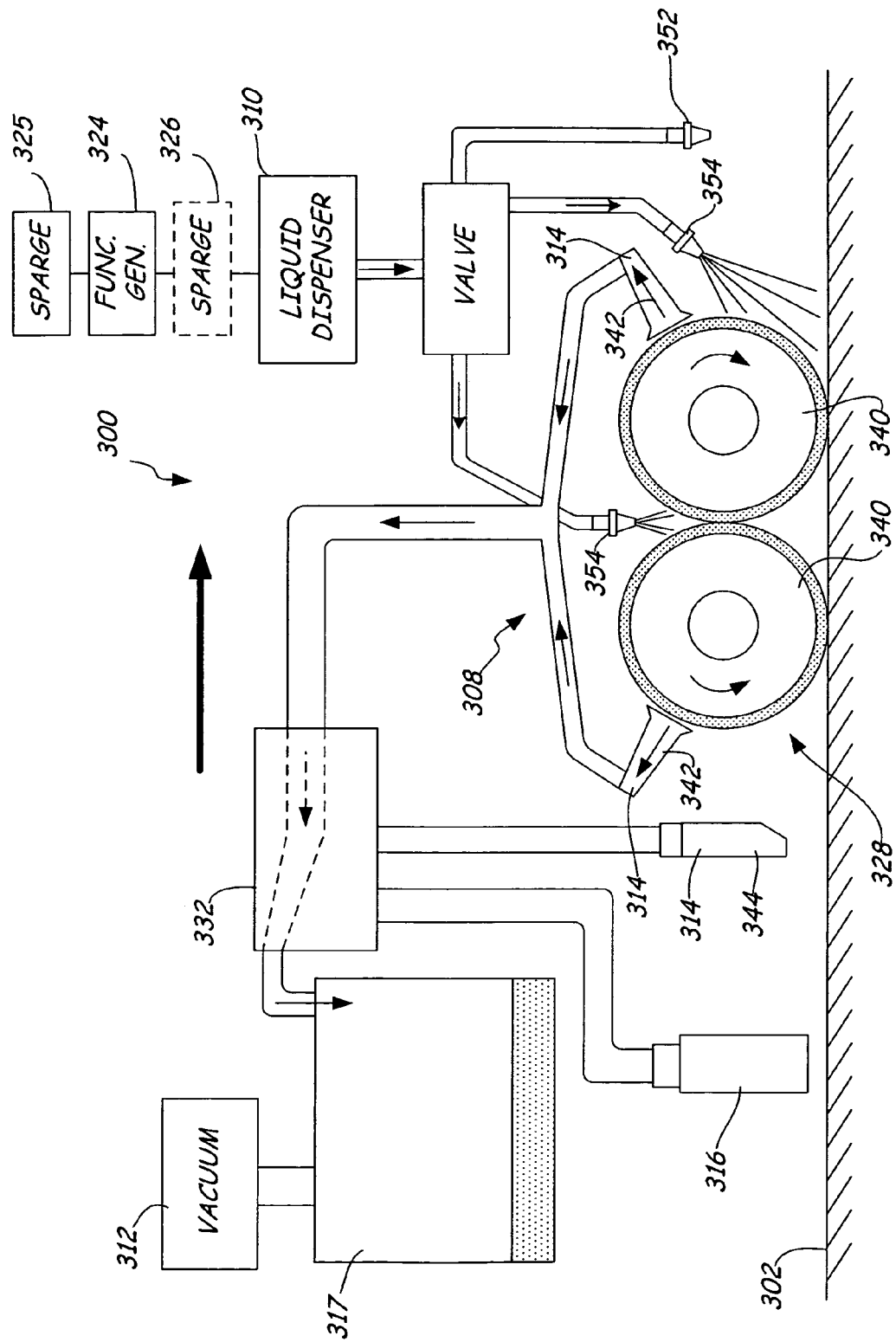
FIG. 13 is a block diagram, which illustrates the cleaner shown in FIG. 12 in a mode adapted to clean soft floors, according to an embodiment of the disclosure.

FIG. 13 is a diagram, which shows cleaning tool 328 in greater detail. In the embodiment shown in FIG. 13, cleaning tool 328 includes one or more soil transfer rolls 340 for cleaning soft floors, and extractor tool 314 includes a roll extractor tool 342. The rolls are rotated by operation of one or more motors 330 (FIG. 12) and wipe the surface 302, which transfers soil from the surface onto soil transfer rolls 340. The rotation of rolls 340 in the directions indicated by the arrows results in portions of the soil transfer rolls being wetted with the cleaning liquid, extracted by roll extractors 340, and wiped against surface 302. For example as the rolls 340 are revolved, they engage the soft floor (e.g., carpet fibers) 302 and cause soil to be transferred from the carpet fibers to the rolls 340. Rolls 340 are further rotated and sprayed again with cleaning liquid by a nozzle 346. Subsequently, the surfaces of rolls 340 are vacuum extracted to remove the soiled cleaning liquid from the rolls, which is conveyed into recovery tank 317. Another embodiment of extractor tool 314 is in the form of a surface extractor tool 348 that is configured to remove liquid and solid waste from surface 302.

Figure 14:
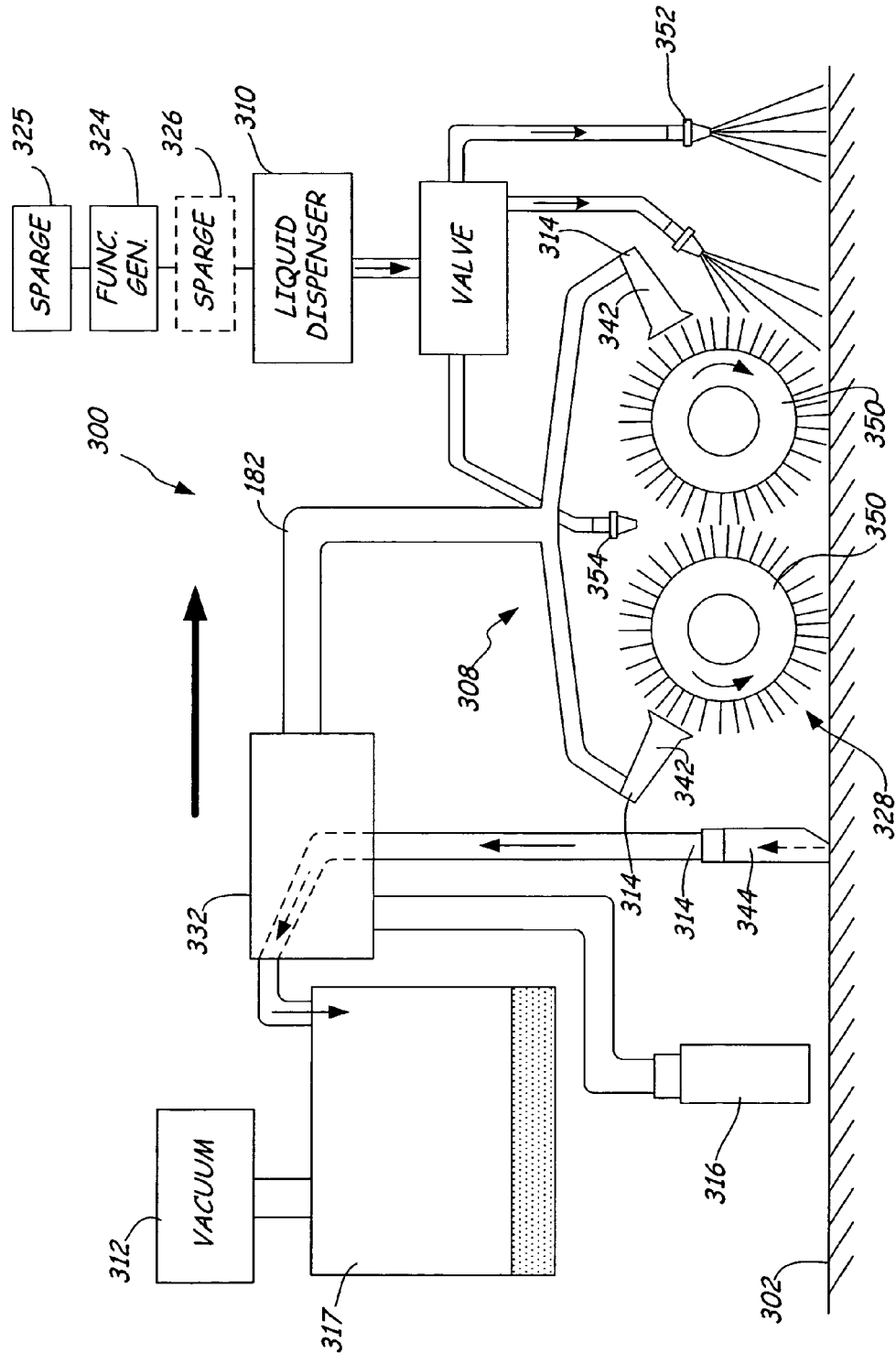
FIG. 14 is a block diagram, which illustrates the cleaner shown in FIG. 12 in a mode adapted to deeply clean soft floors, according to an embodiment of the disclosure.

FIG. 14 illustrates cleaning tool 328 in a deep extraction cleaning mode of operation, in which the cleaner 300 functions similarly to known carpet extractors, except that the cleaning liquid includes EA water and/or sparged water as discussed above. If necessary, soil transfer rolls 340 are replaced with the extractor brushes 350, the cleaning head 308 and the surface extractor 344 are moved to their operating positions, and the vacuum squeegee 316 is moved to the raised position. The liquid dispenser 310 discharges cleaning liquid to surface 302 through nozzle(s) 352 or uses nozzle(s) 354 to direct liquid onto both the surface 302 and the leading extractor brush 350. Extractor brushes 350 are driven via the motor(s) 330 to engage the floor surface 302. As the cleaner 300 progresses across the floor surface 302, surface extractor 344 engages the wetted portion of the surface to remove the soiled liquid from the surface. Also, roll extractor tools 342 remove soiled liquid and debris from brushes 350.

Figure 15:
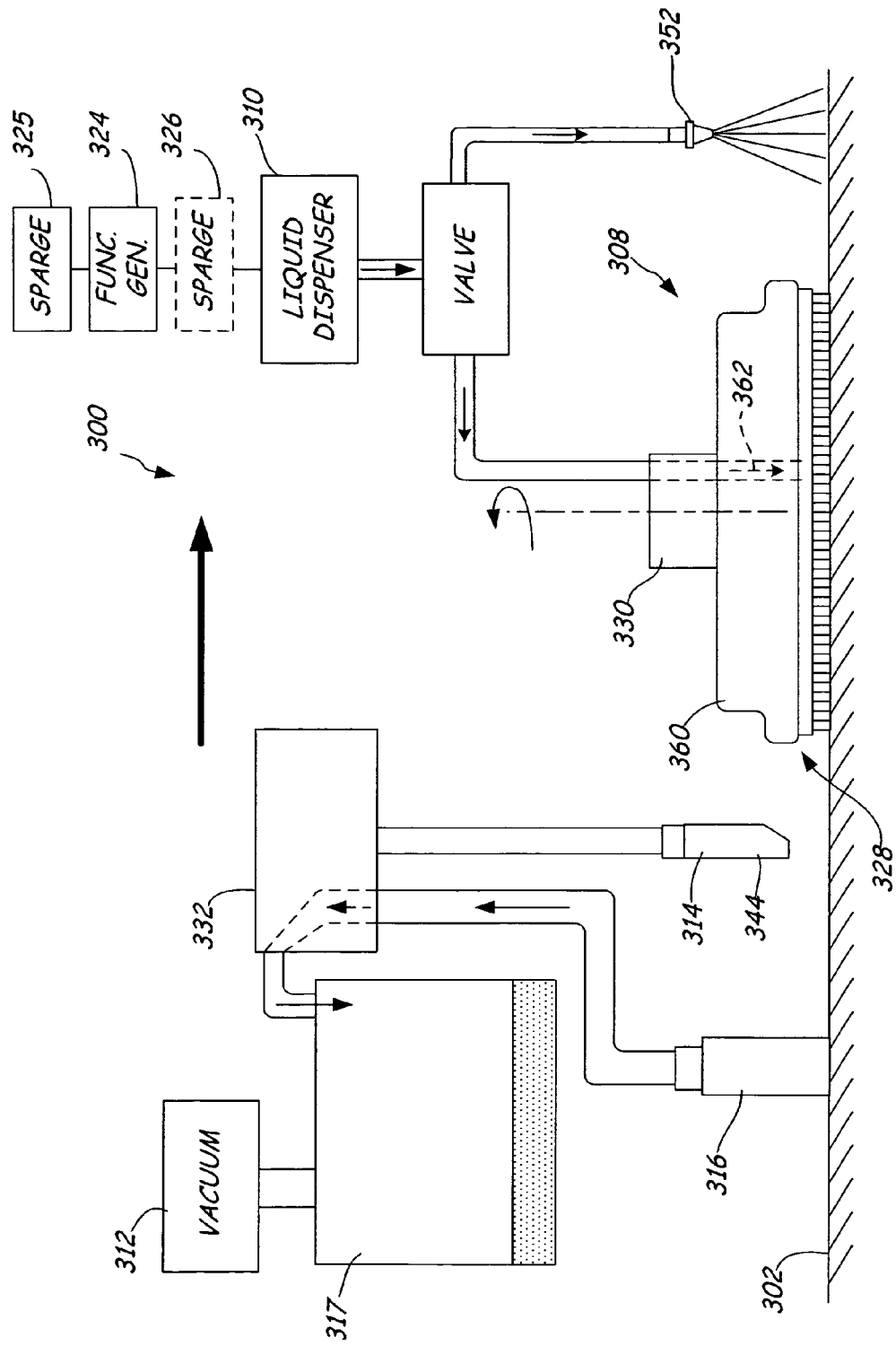
FIG. 15 is a block diagram, which illustrates the cleaner shown in FIG. 5 in a mode adapted to clean hard floors, according to an embodiment of the disclosure.

FIG. 15 illustrates cleaning tool 328 in a hard floor scrubbing mode of operation. Initially, a hard floor scrub brush 360 is installed in a reconfigurable cleaning head 308, or a separate hard floor cleaning head 308 having the scrub brush 360 is attached to the mobile body 306 (FIG. 12). Also, the cleaning head 308 and the vacuum squeegee 316 are moved to their operating positions and the surface extractor tool 344 is moved to the raised position. Next the liquid dispenser 310 wets surface 302 with liquid by discharging the liquid through nozzle 352 and/or wets the surface 302 and scrub brush 360 by discharging liquid 230 through tubing 362 that is internal or external to scrub brush 360. Motor 330 rotates scrub brush 360 as it engages the wetted surface 302. As the cleaner 300 moves in the forward direction, the soiled liquid is collected by squeegee 316 and directed toward waste recovery tank 317.

In a further embodiment, cleaner 300 is constructed similar to a commercially-available multi-mode cleaner from Tennant Company of Minneapolis, Minn. under the trademark READY SPACE®, but is modified to eliminate the traditional detergent supply system and replace it with a sparging device and/or a functional generator similar to one or more of the embodiments described herein. One embodiment of the READY SPACE® cleaner is described in more detail in U.S. Pat. No. 6,735,812, for example, which is incorporated herein by reference.

14. EXAMPLE OF A CARPET EXTRACTOR SYSTEM

Figure 16:
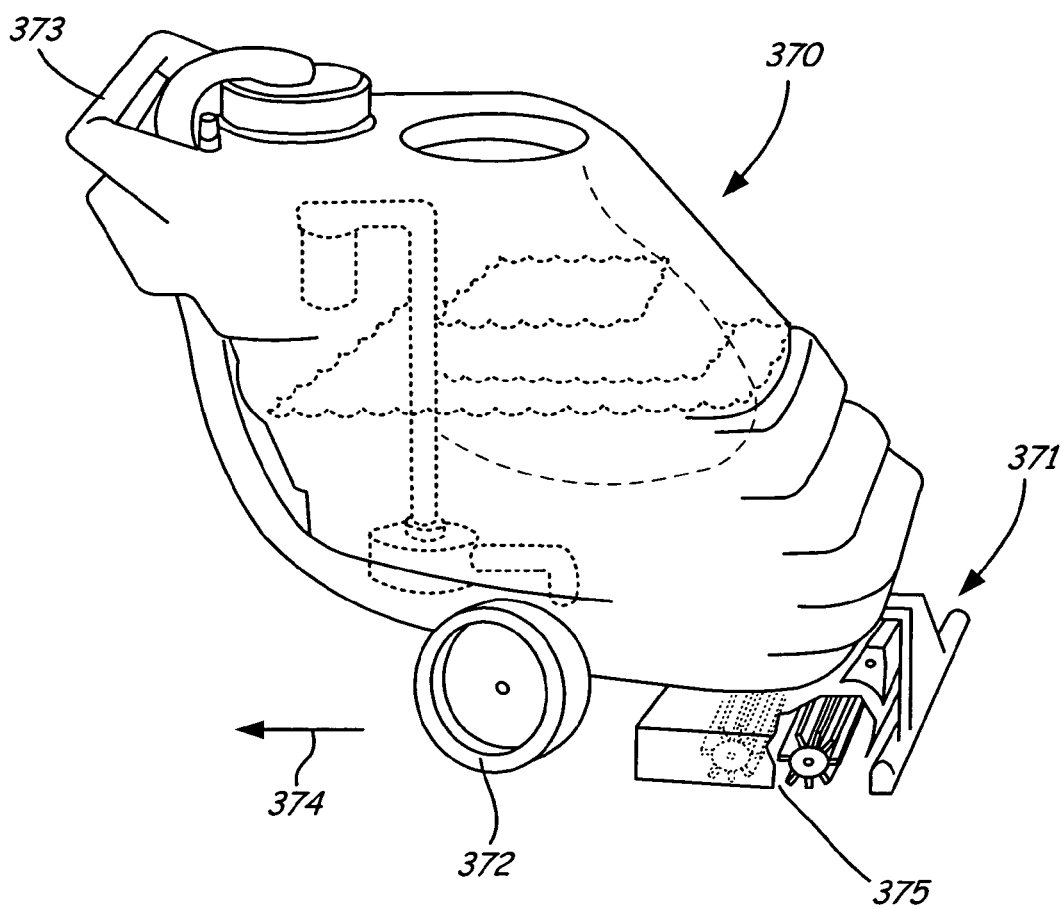
FIG. 16 is a perspective view of a soft floor cleaner (e.g. carpet extractor), according to an embodiment of the disclosure.

FIG. 16 is a perspective view of a carpet extractor machine 370, which has a vacuum pick-up head 371 used to extract at least a part of soiled liquid from carpet and other soft floors. Extractor 370 further includes a pair of wheels 372 and a control handle 373. During operation, an operator pulls extractor 370 rearwards in the direction of arrow 373 as the extractor dispenses a liquid to the floor being cleaned and/or one or more motorized cleaning tools 375. Cleaning tools 375 can include any known soft floor cleaning tool, such as brushs, rollers, bristles, etc. Additional details of extractor 370 are disclosed in U.S. Pat. Nos. 7,059,013 and 4,956,891, which are incorporated herein by reference in their entirety.

Any of the vacuum pick-up heads disclosed therein, for example, can be used in extractor 370. In an exemplary embodiment, extractor 370 can exclude cleaning tool 375 and just dispense the liquid to the floor then extract the soiled liquid from the floor.

Extractor 370 is modified to include a liquid distribution system with a sparging device and/or a functional generator, such as but not limited to that disclosed in FIG. 11 or any of the other embodiments disclosed herein. Extractor 370 can be constructed to deliver and then extract one or more of the following liquids, for example, to and from the floor being cleaned: anolyte EA water, catholyte EA water, sparged anolyte EA water, sparged catholyte EA water, blended anolyte and catholyte EA water and blended sparged anolyte and catholyte EA water, and sparged water. Liquid other than or in addition to water can also be used.

15. EXAMPLE OF AN ALL SURFACE (E.G., BATHROOM) CLEANER

Figure 17:
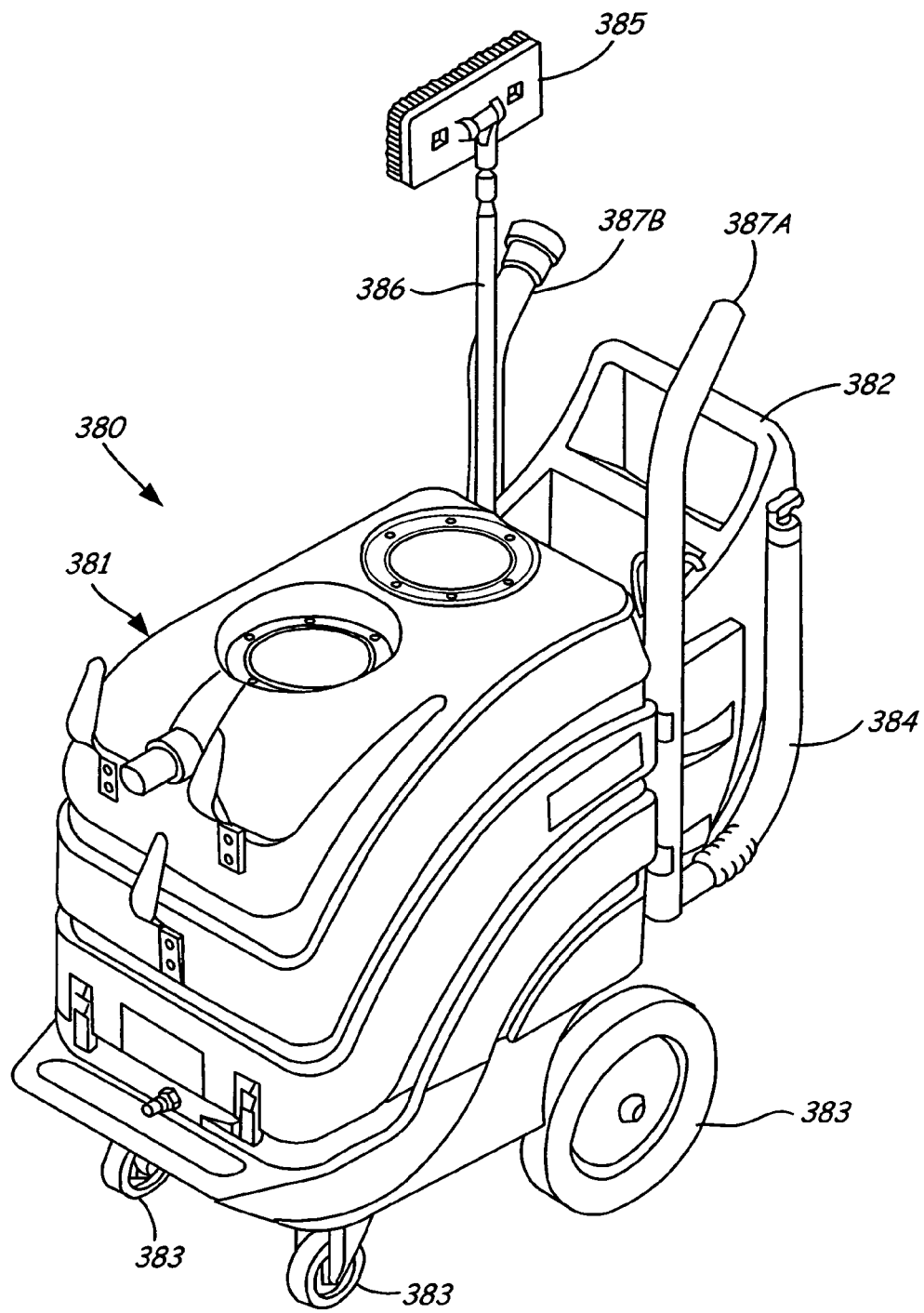
FIG. 17 is a perspective view of an all-surface cleaner, according to an embodiment of the disclosure.

FIG. 17 is a perspective view of an all surface cleaning assembly 380, which is described in more detail in U.S. Pat. No. 6,425,958, which is incorporated herein by reference in its entirety. The cleaning assembly 380 is modified to include a liquid distribution path with one or more sparging devices and/or one or more functional generators such as but not limited to those shown in FIG. 11, for example, or any of the other embodiments disclosed herein.

Cleaning assembly 380 can be constructed to deliver and optionally recover one or more of the following liquids, for example, to and from the floor being cleaned: anolyte EA water, catholyte EA water, sparged anolyte EA water, sparged catholyte EA water, blended anolyte and catholyte EA water and blended sparged anolyte and catholyte EA water, and sparged water. Liquid other than or in addition to water can also be used.

Cleaning assembly 380 can be used to clean hard surfaces in restrooms or any other room having at least one hard surface, for example. Cleaning assembly 380 includes the cleaning device and the accessories used with the cleaning device for cleaning the surfaces, as described in U.S. Pat. No. 6,425,958. Cleaning assembly 380 includes a housing 381, a handle 382, wheels 383, a drain hose 384 and various accessories. The accessories can include a floor brush 385 having a telescoping and extending handle 386, a first piece 387A and a second piece 387B of a two piece double bend wand, and various additional accessories not shown in FIG. 17, including a vacuum hose, a blower hose, a sprayer hose, a blower hose nozzle, a spray gun, a squeegee floor tool attachment, a gulper tool, and a tank fill hose (which can be coupled to ports on assembly 380). The assembly has a housing that carries a tank or removable liquid container and a recovery tank or removable recovery liquid container. The cleaning assembly 380 is used to clean surfaces by spraying the cleaning liquid through a sprayer hose and onto the surfaces. The blower hose is then used to blow dry the surfaces and to blow the fluid on the surfaces in a predetermined direction. The vacuum hose is used to suction the fluid off of the surfaces and into the recovery tank within cleaning device 380, thereby cleaning the surfaces. The vacuum hose, blower hose, sprayer hose and other accessories used with cleaning assembly 380 can be carried with the cleaning device 380 for easy transportation.

In some embodiments, the output flow may be very high, such as with a sprayer. If the output flow rate of a particular tool or apparatus exceeds the rate at which the functional generator or sparging device is capable of effectively treating the liquid to be sprayed, the apparatus can be configured to include one or more output reservoirs for containing the produced anolyte and catholyte (either separately or combined) until needed. Once primed with output liquid, the output reservoirs can provide a buffer that can supply a higher output flow rate.

16. EXAMPLE OF A TRUCK-MOUNTED CLEANING SYSTEM

Figure 18:
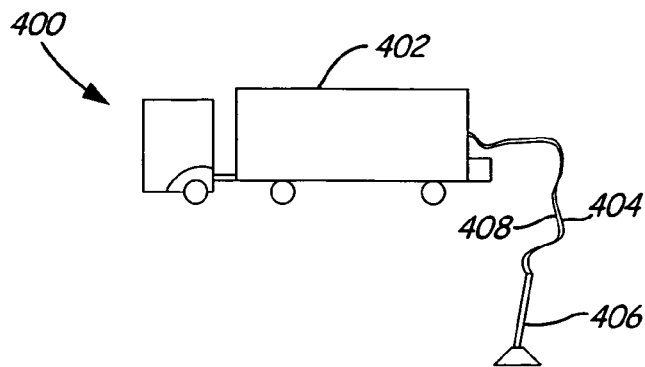
FIG. 18 is a diagram illustrating a truck-mounted system according to a further embodiment of the disclosure.

FIG. 18 is a diagram illustrating a truck-mounted system 400 according to a further embodiment of the disclosure. A cleaning system, with one or more of the components of the embodiments discussed herein, such as those shown in FIG. 11, is mounted within truck 402. Using the reference numbers shown in FIG. 11, truck 402 carries a source tank 106 for containing liquid, such as regular tap water, an onboard functional generator 162 and one or more sparging devices 161 and/or 163 for electrochemically activating and sparging the water. Alternatively, for example, the sparging device(s) and/or the functional generator can be eliminated. The liquid distribution system includes one or more hoses 404, which pass the electrochemically activated water (e.g., sparged anolyte EA water and/or sparged catholyte EA water) to a cleaning wand 406, which dispenses the water onto the surface being cleaned. Cleaning wand 406 can further include an extractor, which is coupled by a hose 408 to a vacuum source that is also carried by truck 402. As the operator passes the cleaning end of wand 406 over the surface to be cleaned, the wand dispenses the EA water onto the surface while the extractor recovers soiled water and debris from the surface.

In a further embodiment, a wand similar to wand 406 can be implemented on any of the cleaners shown or discussed with reference to any of the figures herein, with or without additional cleaning or extraction tools or recovery systems.

17. ODORANT

Figure 19:
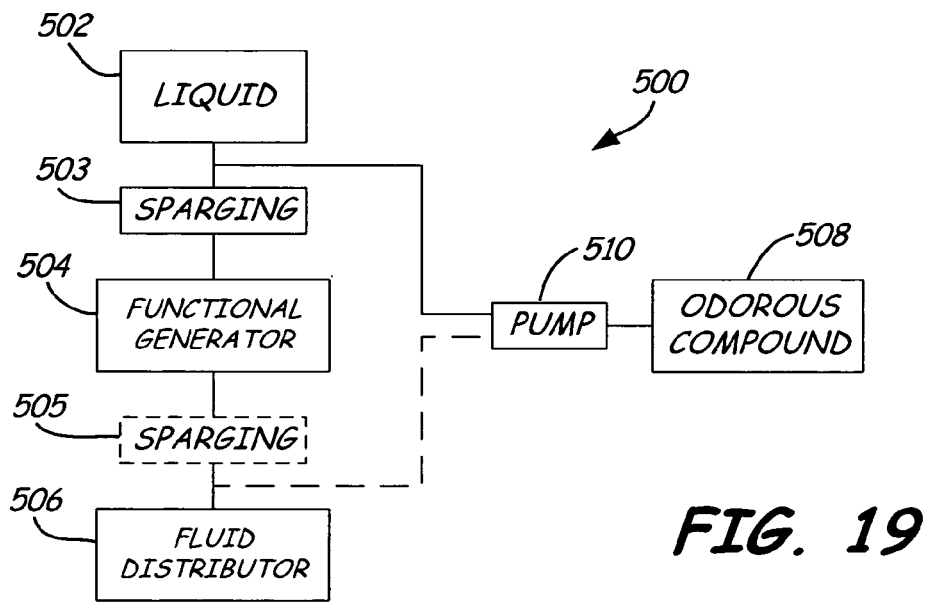
FIG. 19 is a simplified block diagram, which illustrates a cleaner having an EA water distribution system with an odorous compound source according to a further embodiment of the disclosure.

FIG. 19 is a simplified block diagram, which illustrates a mobile or immobile cleaner 500 having an EA water distribution system according to a further embodiment, which could be implemented in any of the embodiments discussed herein. In one embodiment, the distribution system includes a source of liquid 502, a sparging device 503, a functional generator 504, a sparging device 504 and a fluid dispenser 506. In addition, cleaning system 500 includes a source of an odorous compound 508, which can be drawn into the liquid flow path by a dispersion pump 510 either upstream or downstream of functional generator 504. Other apparatus and methods can also be used to disperse the odorous compound in the liquid. For example, the odorous compound can be formed in the shape of a long lasting puck that can be placed in the flow path and dissolves slowly. Also, one or more of the sparging device 503, functional generator 504 or sparging device 505 can be eliminated in other embodiments.

The odorous compound adds an aroma or odor to the liquid affects, stimulates, or is perceived by the sense of smell of the user. For example, such an aroma could include a readily selectable scent that could be perceived by the user to indicate that the surface is clean. The scent could be "fresh", "sharp" or "citrus", for example. Other scents can also be used for other effects, such as for aroma therapy or for matching a situation in which the processed floor or surface is used. For example, a tropical scent can be used to match a tropical decor. The user of the cleaner can choose an appropriate scent for the situation.

However, it has been found that one or more of the cleaning devices disclosed herein already provide a naturally "clean"

scent without the use of an extra odorous compound 508 due to the meta-stable reactive species that may be produced by the functional generator, such as chlorine.

18. CLEANING LIQUID GENERATOR

Figure 20:
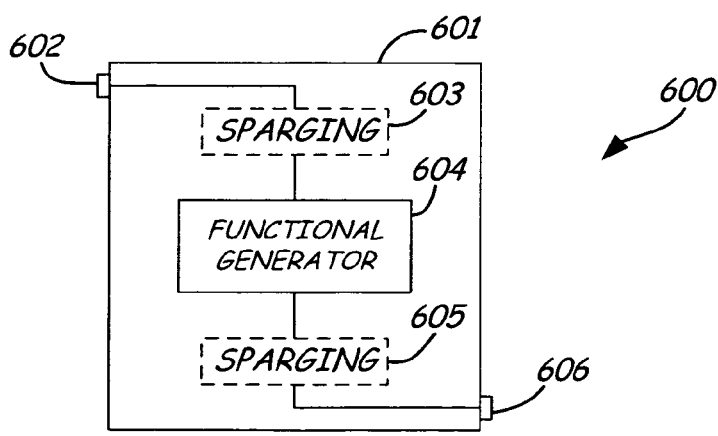
FIG. 20 is a simplified block diagram of a cleaning liquid generator that mounted to a platform according to another embodiment.

FIG. 20 is a simplified block diagram of a cleaning liquid generator 600 that is mounted to a platform 601 according to an exemplary embodiment. Platform 601 can be configured to be mounted or placed in a facility on a floor, a wall, a bench or other surface, held by hand, carried by an operator or vehicle, attached on to another device, be held by hand, or carried on a person, etc. For example, platform 601 can be carried by a cleaning or maintenance trolley or mop bucket. Platform 601 includes an inlet 602 for receiving a liquid, such as tap water, from a source. Alternatively, for example, platform 601 can include a tank for holding a supply of liquid to be treated. Platform 601 further includes a sparging device 603, a functional generator 604 and a further sparging device 605. In an embodiment, platform 601 includes only one of the sparging devices 603 or 605. In a further embodiment, both sparging devices 603 and 605 are eliminated. The output of sparging device 605 (or functional generator 604, is coupled to an outlet 606. Platform 601 can also include any of the other devices or components such as but not limited to those disclosed herein.

The flow paths from the output of functional generator 604 can be configured to dispense anolyte EA liquid only, catholyte EA liquid only, both anolyte EA liquid and catholyte EA liquid, or blended anolyte and catholyte EA liquid. Unused anolyte or catholyte can be directed to a waste tank on platform 601 or to a drain outlet, for example. In embodiments in which both anolyte and catholyte EA are dispensed through outlet 606, the outlet can have separate ports or a combined port, which delivers a blended mixture of catholyte and anolyte, for example, as discussed with reference to FIG. 11. Further, any of the embodiments herein can include a storage tank for containing the produced liquid at the output of the dispenser. Also, one or more of the sparging device 603, functional generator 604 or sparging device 605 can be eliminated in other embodiments.

In a further embodiment, platform can be incorporated into or on a spray bottle, such as a hand-triggered spray bottle, wherein the spray bottle contains a liquid to be sprayed on a surface and the functional generator converts the liquid to an anolyte EA liquid and a catholyte EA liquid prior to dispensing the converted liquid as an output spray. The anolyte and catholyte EA liquids can be dispensed as a combined mixture or as separate spray outputs. With a small and intermittent output flow rate provided the spray bottle, the functional generator can have a small package and be powered by batteries carried by the package or spray bottle, for example.

19. OXIDATION-REDUCTION POTENTIAL INDICATOR

Another aspect of the disclosure relates to a method and apparatus for providing a user with a humanly-perceptible indication of the oxidation-reduction potential of EA liquid, such as but not limited to the EA liquid generated or used in any of the embodiments discussed herein. For example, the mobile hard and/or soft floor surface cleaners discussed with respect to FIGS. 10-17 can be modified to include an onboard functional generator and a visual or audible indicator of the output liquid's oxidation-reduction potential. Similarly, any of the apparatus shown or described with reference to any of the other figures can be modified to further include such an indicator.

The indicator can include a measurement instrument having an analog or digital scale, an indicator light, a dial or a sound output, or can include a change in a perceptible property of the liquid such as its color. For example, a dye can be injected into the liquid based on an output of a measurement instrument or the color change can be triggered by a chemical response of an additive within the liquid to the oxidation-reduction potential of the liquid. For example certain metal ions can change the water color as a function of the water's oxidation-reduction potential.

In a further embodiment, the indicator provides a machine-readable analog or digital output as a function of the oxidation-reduction potential. The apparatus can include electrical hardware and software for providing a respective output signal of any type, for monitoring the oxidation-reduction potential, and/or for storing a history of the oxidation-reduction potential and any other desired indicators that reflect an operating state or condition of the apparatus. In one embodiment, the apparatus monitors the amount of EA water being used, the status of the apparatus, and the oxidation-reduction potential of the output liquid. If the oxidation-reduction potential is not within a desired range or if another error condition occurs on the apparatus, this event can be logged on the apparatus and reported to the user of the machine or transmitted to local or remote maintenance personnel through a suitable output and transmission media. For example, a local monitoring system can receive the transmission and send a corresponding report to maintenance personnel through an email message. Other maintenance events can also be logged and reported for triggering automatic maintenance steps.

Also, EA liquid usage can be automatically logged on the apparatus and transmitted to a local or remote monitoring system for billing purposes.

In a further embodiment, the apparatus can monitor, log and/or report the status and functioning states of the sparging devices through any of the above methods. The apparatus can measure, log and report time of operation for purposes of scheduling certain maintenance procedures at predetermined intervals. For example, in embodiments in which one or more of the electrodes in the functional generator or sparging devices emit ions, such as silver ions, a measure of the total time of use since the electrode was installed can be used to schedule replacement before the end of the electrode's useful life or to notify the user through an indicator.

20. VISUAL INDICATOR REPRESENTING OPERATION OF FUNCTIONAL GENERATOR

Another aspect of the disclosure relates to a method and apparatus for providing a user with a humanly-perceptible indication of the electrical operation of the functional generator or the sparger. The level of power consumed by the function generator (and/or sparger) can be used to determine whether the functional generator is operating correctly and therefore whether the liquid (EA anolyte and/or EA catholyte) produced by the generator is electrochemically activated to a sufficient level. Power consumption below a reasonable level can reflect various potential problems such as use of ultra-pure feed water or feed water having a generally low electrolyte content (e.g., low sodium/mineral content) such that the water does not conduct a sufficient level of electrical current within the functional generator. The current consumption can therefore also indicate high or low levels of oxidation-reduction potential, for example.

For example, the mobile hard and/or soft floor surface cleaners discussed with respect to FIGS. 10-17 can be modified to include an onboard functional generator and a visual, audible or tactile indicator that is representative of the power consumed by the functional generator. Similarly, any of the apparatus shown or described with reference to any of the other figures can further include such an indicator.

Figure 21:
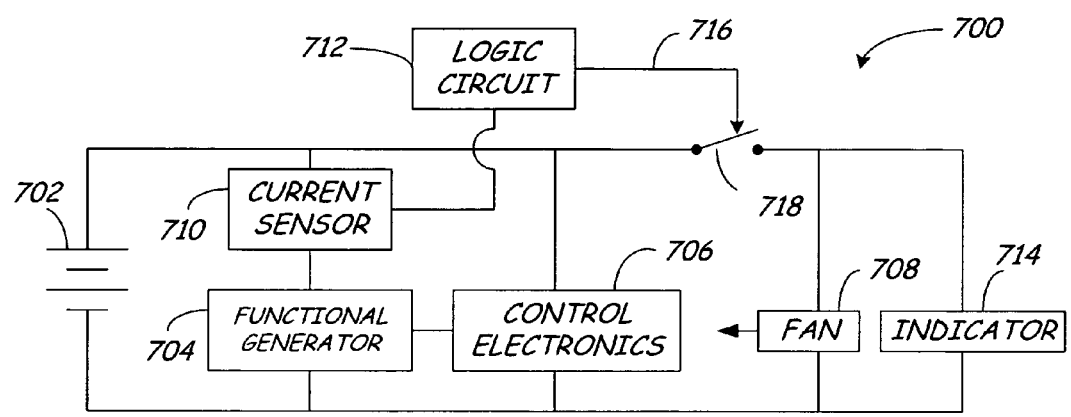
FIG. 21 is a block diagram of a system, which includes an indicator representing an operating state of a functional generator.

FIG. 21 is a block diagram of a system 700 having an indicator according to an embodiment of the disclosure, which can be incorporated into any of the embodiments disclosed herein, for example. System 700 includes power supply 702, functional generator (and/or sparger) 704, control electronics 706, cooling fan 708, current sensor, 710, logic circuit 712 and indicator 714. For simplicity, the liquid inputs and outputs of functional generator 704 are not shown in FIG. 21. All elements of system 700 can be powered by the same power supply 702 or by two or more separate power supplies, for example.

Control electronics 706 are coupled to control the operating state of functional generator 704 based on the present operating mode of system 700 and user control inputs, such as those received from control unit 146 of cleaner 100 shown in FIGS. 10A-10C. Control electronics 706 can correspond to the control electronics 64 in the embodiment shown in FIG. 8A, for example. Cooling fan 708 can be provided to cool control electronics 706 and can be attached to a housing containing functional generator 704 and control electronics 706, for example.

The power consumed by functional generator 710 can be monitored through current sensor 710, which can be coupled in electrical series with functional generator 704 and power supply 702. Current sensor 710 provides an analog or digital output 716 that is representative of the current flowing through the functional generator. Logic circuit 712 compares output 716 to predetermined threshold current levels or ranges and then operates indicator 714 as a function of the comparison. The threshold current levels or ranges can be selected to represent predetermined power consumption levels, for example.

Indicator 714 can include an indicator light, a dial, a sound output, a tactile output, a measurement instrument having an analog or digital scale, or any other perceptible output. In one embodiment, shown in more detail below with respect to FIG. 22, fan 708 is a lighted fan comprising one or more colored lights (e.g., LEDs) that are electrically coupled in parallel with the fan motor, as shown in FIG. 21. When operated by logic circuit 712 through switch 718, the lights function as indicator lights representative of the operating state of functional generator 704. However, the indicator lights can be operated by logic circuit 712 independently of the fan motor in other embodiments.

In one illustrative embodiment, logic circuit 712 operates the indicator lights 714 as a function of the current level sensed by current sensor 710. For example, logic circuit 712 can turn off (or alternatively, turn on) the indicator lights as a function of whether the current level sensed is above or below a threshold level. In one embodiment, logic circuit 712 operates the indicator lights in a steady "on" state when the sensed current level is above the threshold level, and cycles the indicator lights between the "on" state and an "off" state at a selected frequency to indicate a problem when the sensed current level is below the threshold level. Multiple threshold levels and frequencies can be used in other embodiments. Also, indicator 714 can include a plurality of separately-controlled indicators, such as a plurality of lights, each indicating operation within a predefined range. Alternatively or in addition, logic circuit can be configured to alter the illumination level of one or more indicator lights as a function of the sensed current level relative to one or more thresholds or ranges, for example.

In the embodiment shown in FIG. 10C, the top of housing 150 includes a cooling fan 708 for cooling the control electronics of the functional generator and sparger. In this embodiment, the cooling fan included a Mad Dog MD-80MM-4LED-F type 80 mm color fan, which includes four blue LED lights to illuminate the fan assembly when the fan is powered and the fan blades are spinning at approximately 2000 RPM. This type of fan is typically used for gaming computer systems for cooling and illumination of a clear computer case that houses the computer hardware. Other types of lighted fans can be used in other embodiments.

In embodiment shown in FIG. 10C, the fan motor and LEDs are electrically coupled in parallel with one another as shown in FIG. 21. The fan motor and LEDs are therefore turned on and off together under the control of logic circuit 712. However, the fan motor and the LEDs can be controlled independently as mentioned above. The lighted fan provides a simple means of visually indicating the health of the functional generator. To the user, the steady glow of the indicator light provides assurance that the water being applied to the surface being cleaned is in fact electrochemically activated.

FIG. 10B illustrates cleaner 100 with the lid 104 of the cleaner is closed on top of base 102. Due to the placement of the functional generator near a gap between lid 104 and base 102, the steady glow of the cooling fan LEDs, represented by arrows 720, is visible in an area along the side of the cleaner, during normal operation. However, the indicator light can be positioned at any other location, either with the fan motor or remote from the fan motor.

In another embodiment, indicator 714 can be located at any location on the device in which system 700 is incorporated. For example, indicator 714 can include one or more a light emitting diodes attached to the user control panel of cleaner 100 shown in FIGS. 10A-10C. Alternatively, for example, indicator 714 can be located within or on a housing of cleaner 100.

In a further embodiment, logic circuit 712 can store a history of the current level or consumed power and any other desired indicators that reflect an operating state or condition of the apparatus. In one embodiment, if the consumed power is not within a desired range or if another error condition occurs on the apparatus, this event can be logged on the apparatus and reported to the user of the machine or transmitted to local or remote maintenance personnel through a suitable output and transmission media. For example, a local monitoring system can receive the transmission and send a corresponding report to maintenance personnel through an email message. Other maintenance events can also be logged and reported for triggering automatic maintenance steps.

In yet another embodiment, the indicator includes a tactile indicator, such as a vibrator, which vibrates and element of the cleaner when the power consumed by the functional generator is outside a desired range or below some threshold. For example, in the embodiment shown in FIGS. 10A-10C, the tactile indicator can vibrate control handle 148 or wheels 118 or 119. In an embodiment that includes a seat for the operator, the tactile indicator can selectively vibrate the seat upon an error condition.

21. OUTPUT LIQUID

In an exemplary embodiment, a sparged reaction product is provided, which is produced at least in part from water being in contact with an anode and a cathode, the anode and cathode being separated by a membrane that permits one-way transport across the membrane of selected ions generated by the cathode or anode.

For example, the reaction product may include tap water or may consist essentially of water. Other fluids can also be used. The reaction product can include a combination of an anolyte and a catholyte, as discussed above. The catholyte may be characterized by a stochiometric excess of hydroxide ions, for example.

In a further exemplary embodiment, a reaction product is provided, which is produced from a combination of water being in contact with an anode and water being in contact with a cathode, the anode and cathode being separated by a membrane that permits one-way transport across the membrane of selected ions generated by the cathode or anode.

For example, the membrane permits one-way transport of hydroxide ions towards the cathode, the hydrogen ions having been generated by the anode, and wherein the membrane permits transport across the membrane of ions generated by the cathode towards the anode. The reaction product can include, for example, an anolyte produced by the anode and a catholyte produced by the cathode, wherein the catholyte is characterized by a stochiometric excess of hydroxide ions.

In a further exemplary embodiment, a combined anolyte and catholyte electrochemically activated fluid is provided. For example, the fluid can include tap water or can consist essentially of water. Other fluids can also be used.

22. CONCLUSION

With no added surfactant or detergent, one or more embodiments provide a cleaning system that is purely non-chemical and has the ability to use typical tap water that has been electrochemically activated as the primary or sole liquid while providing effective cleaning and/or sanitizing properties. However, surfactants or detergents can be added if desired. Also, the addition of sparging upstream and/or downstream of the functional generator can further enhance the cleaning or sanitizing properties of the output liquid and production efficiency. The system can therefore provide an effective environmental solution for cleaning residential, industrial, commercial, hospital, food processing, and restaurant facilities and more. The cleaning system can be mobile or immobile.

Also, when tap water has been electrochemically activated as the sole cleaning liquid when used in a cleaning and/or sanitizing system, no de-foaming chamber would be required in the recovery tank of a hard or soft floor scrubbing machine.

Although the present invention has been described with reference to preferred embodiments, workers skilled in the art will recognize that changes may be made in form and detail without departing from the spirit and scope of the invention. Also, the term "coupled" as used in the specification and claims can include a direct connection or a connection through one or more intermediate elements.

What is claimed is:

1. A mobile surface cleaner comprising:
    a mobile body configured to travel over a surface;
    a source of a liquid;
    a liquid dispenser;
    a flow path from the liquid source to the liquid dispenser;
    an electrolyzing sparging device in fluid communication with the flow path and which lacks an ion exchange membrane;
    a functional generator in the flow path, which comprises an anode chamber and a cathode chamber separated by an ion exchange membrane and which electrochemically activates at least one of the liquid from the source or sparged liquid from the sparging device, wherein a flow of the liquid from the anode chamber is combined with a flow of the liquid from the cathode chamber along the flow path, or at the liquid dispenser to form a combined flow, or a combination thereof, which is dispensed from the liquid dispenser; and
    a control circuit which applies power to the sparging device and the functional generator such that the sparging device is operable to generate nanobubbles in the liquid by electrolysis, wherein the nanobubbles have a size that is too small to break surface tension of the liquid.

2. The mobile surface cleaner of claim 1, wherein the electrolyzing sparging device comprises:
    first and second electrically conductive electrodes, which are separated by a gap, wherein the flow path is in fluid communication with the gap.

3. The mobile surface cleaner of claim 2, wherein:
    at least one of the first or second electrodes is tubular; and
    the first and second electrodes are coaxial with one another.

4. The mobile surface cleaner of claim 3, wherein the electrolyzing sparging device further comprises:
    a tubular dielectric mesh positioned in the gap between the first and second electrodes, and wherein one of the first and second electrodes comprises a solid tubular metallic plate and the other electrode comprises a tubular metallic mesh.

5. The mobile surface cleaner of claim 2, wherein the first and second electrodes are planar.

6. The mobile surface cleaner of claim 1, wherein:
    the liquid source comprises a tank; and
    the electrolyzing sparging device is coupled in the flow path, between the tank and the liquid dispenser.

7. The mobile surface cleaner of claim 1, wherein:
    the liquid source comprises a tank; and
    the electrolyzing sparging device is located at least partially within the tank.

8. The mobile surface cleaner of claim 1 wherein the electrolyzing sparging device comprises:
    first and second electrically conductive electrodes, which are separated by a gap.

9. The mobile surface cleaner of claim 1 wherein the liquid source comprises a tank to carry a supply of the liquid and wherein the cleaner further comprises:
    a pump in fluid communication with the flow path.

10. The mobile surface cleaner of claim 9, wherein the control circuit is configured to operate the sparging device and the functional generator on-demand and comprises:
    a first operating mode during motion of the cleaner relative to the surface being cleaned, during which the control circuit energizes the pump to pump the liquid along the flow path, energizes the electrolyzing sparging device to sparge the liquid that is passed through the sparging device, energizes the functional generator to activate at least one of the liquid from the source or the sparged liquid from the sparging device, and delivers sparged, electrochemically activated liquid to the surface by the liquid dispenser; and
    a second operating mode when the cleaner is at rest relative to the surface being cleaned, during which the control circuit de-energizes the pump to terminate flow of the liquid along the flow path and de-energizes the electrolyzing sparging device and the functional generator.

11. The mobile surface cleaner of claim 1 wherein the liquid source comprises a tank carried by the cleaner and wherein the cleaner further comprises:

a motorized cleaning head connected to the mobile body and comprising a cleaning tool;
a pump in fluid communication with the flow path, wherein the liquid dispenser is configured to apply sparged liquid to at least one of the elements of the group comprising the surface, the cleaning tool or both the surface and the cleaning tool; and
a fluid recovery device connected to the mobile body.

12. The mobile surface cleaner of claim 11, wherein the cleaning tool comprises a hard floor surface cleaning tool and the fluid recovery device comprises a vacuum squeegee connected to the mobile body to engage the surface.

13. The mobile surface cleaner of claim 12, wherein the hard floor surface cleaning tool comprises a hard floor scrub brush.

14. The mobile surface cleaner of claim 11, wherein:
the cleaning tool comprises a soft floor surface cleaning tool comprising a soil transfer roller or a soft floor extraction tool; and
the fluid recovery device comprises a vacuum extractor configured to remove liquid from at least one of the surface being cleaned or the cleaning tool.

15. A mobile surface cleaner comprising:
a mobile body configured to travel over a surface;
a tank carried by the mobile body;
a motorized cleaning head connected to the mobile body and comprising a cleaning tool;
a liquid dispenser;
a flow path from the tank to the liquid dispenser;
an electrolyzer onboard the cleaner, which sparges the liquid by electrolysis and comprises first and second electrically conductive electrodes, which are separated by a gap in fluid communication with the flow path and wherein the gap lacks an ion exchange membrane, wherein the electrolyzer is operable to generate nanobubbles in the liquid by electrolysis, which have a size that is generally too small to break surface tension of the liquid; and
a functional generator in the flow path, which comprises an anode chamber and a cathode chamber separated by an ion exchange membrane and which electrochemically activates at least one of the liquid from the liquid source or the sparged liquid from the electrolyzer.

16. The mobile surface cleaner of claim 15, wherein:
at least one of the first or second electrodes is tubular; and
the first and second electrodes are coaxial with one another.

17. The mobile surface cleaner of claim 16, wherein:
one of the first and second electrodes comprises a solid tubular metallic plate and the other electrode comprises a tubular metallic mesh.

18. The mobile surface cleaner of claim 15, wherein the first and second electrodes are planar.

19. The mobile surface cleaner of claim 15, wherein:
the electrolyzer is coupled in the flow path, between the tank and the liquid dispenser.

20. The mobile surface cleaner of claim 15, wherein:
the electrolyzer is located at least partially within the tank.

21. The mobile surface cleaner of claim 15 and further comprising:
a pump in fluid communication with the flow path.

22. The mobile surface cleaner of claim 21, wherein the cleaner comprises a control circuit, which is configured to operate the sparging device and the functional generator on-demand and comprises:
a first operating mode during motion of the cleaner relative to the surface being cleaned, during which the control circuit energizes the pump to pump the liquid along the flow path and the cleaner energizes the electrolyzer to sparge the liquid from the source of the liquid that is passed through the electrolyzer, energizes the functional generator to activate at least one of the liquid from the source or the sparged liquid from the electrolyzer, and delivers sparged, electrochemically activated liquid to the surface by the liquid dispenser; and
a second operating mode when the cleaner is at rest relative to the surface being cleaned, during which the control circuit de-energizes the pump to terminate flow of the liquid along the flow path and de-energizes the electrolyzer and the functional generator.

23. The mobile surface cleaner of claim 15 wherein cleaner further comprises:
a pump in fluid communication with the flow path, wherein the liquid dispenser is configured to apply the sparged liquid to at least one of the elements of the group comprising the surface, the cleaning tool or both the surface and the cleaning tool; and
a fluid recovery device connected to the mobile body.

24. The mobile surface cleaner of claim 23, wherein the cleaning tool comprises a hard floor surface cleaning tool and the fluid recovery device comprises a vacuum squeegee connected to the mobile body to engage the surface.

25. The mobile surface cleaner of claim 24, wherein the hard floor surface cleaning tool comprises a hard floor scrub brush.

26. The mobile surface cleaner of claim 23, wherein:
the cleaning tool comprises a soft floor surface cleaning tool comprising a soil transfer roller or a soft floor extraction tool; and
the fluid recovery device comprises a vacuum extractor configured to remove liquid from at least one of the surface being cleaned or the cleaning tool.

27. A mobile surface cleaner comprising:
a mobile body configured to travel over a surface;
a source of a liquid;
a liquid dispenser;
a flow path from the liquid source to the liquid dispenser;
means for sparging onboard the cleaner, which sparges the liquid by electrolysis without an ion exchange membrane to generate nanobubbles in the liquid that have a size that is generally too small to break surface tension of the liquid; and
functional generator means in the flow path, which comprises an anode chamber and a cathode chamber separated by an ion exchange membrane for electrochemically activating at least one of the liquid from the source or sparged liquid from the means for sparging.

28. A mobile surface cleaner comprising:
a mobile body configured to travel over a surface;
a source of a liquid;
a liquid dispenser;
a flow path from the liquid source to the liquid dispenser;
an electrolyzing sparging device in fluid communication with the flow path, which comprises first and second electrically conductive, coaxial electrodes, which are separated by a gap that lacks an ion exchange membrane, wherein the flow path is in fluid communication with the gap, a tubular dielectric mesh positioned in the gap between the first and second electrodes, and wherein at least one of the first and second electrodes comprises a tubular metallic mesh;
a functional generator in the flow path, which comprises an anode chamber and a cathode chamber separated by an ion exchange membrane and which electrochemically activates sparged liquid from the sparging device; and a control circuit which applies power to the sparging device and the functional generator such that the sparging device is operable to generate nanobubbles in the liquid by electrolysis, wherein the nanobubbles have a size that is too small to break surface tension of the liquid.

29. A mobile surface cleaner comprising:
a mobile body configured to travel over a surface;
a source of a liquid;
a liquid dispenser;
a flow path from the liquid source to the liquid dispenser;
an electrolyzing sparging device in fluid communication with the flow path;
a functional generator in the flow path, which comprises an anode chamber and a cathode chamber separated by an ion exchange membrane; and
a control circuit which applies power to the sparging device such that the sparging device is operable to generate nanobubbles in the liquid by electrolysis, and wherein the nanobubbles have a size that is too small to break surface tension of the liquid.

30. An apparatus comprising:
a source of a liquid;
a liquid dispenser;
a flow path from the liquid source to the liquid dispenser;
an electrolyzing sparging device in fluid communication with the flow path and comprising first and second electrically conductive electrodes, which are separated by a gap that lacks an ion exchange membrane;
a functional generator in the flow path, which comprises an anode chamber and a cathode chamber separated by an ion exchange membrane and which electrochemically activates at least one of the liquid from the source or sparged liquid from the sparging device; and
a control circuit which applies power to the sparging device and the functional generator such that the sparging device is operable to generate nanobubbles in the liquid by electrolysis, and wherein the nanobubbles have a size that is too small to break surface tension of the liquid.

* * * * *